United States Patent
Heotis et al.

(10) Patent No.: US 11,911,074 B2
(45) Date of Patent: Feb. 27, 2024

(54) DEVICE FOR EXTERNAL FIXATION STRUT MEASUREMENT AND REAL-TIME FEEDBACK

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Charles Heotis, Cordova, TN (US); Johnny Mason, Cordova, TN (US); Andrew Noblett, Cordova, TN (US); Paul Bell, Cordova, TN (US); Nathaniel Kelley Grusin, Cordova, TN (US); Joseph Ferrante, Cordova, TN (US)

(73) Assignees: Smith & Nephew, Inc., Memphis, TN (US); Smith & Nephew Pte. Limited Smith, Singapore (SG); Nephew Orthopaedic.; AG, Zug (CH)

( * ) Notice: Subject to any disclaimer, the term of this patent is extended or adjusted under 35 U.S.C. 154(b) by 194 days.

(21) Appl. No.: 17/424,324

(22) PCT Filed: Jan. 29, 2020

(86) PCT No.: PCT/US2020/015558
§ 371 (c)(1),
(2) Date: Jul. 20, 2021

(87) PCT Pub. No.: WO2020/160076
PCT Pub. Date: Aug. 6, 2020

(65) Prior Publication Data
US 2022/0071662 A1    Mar. 10, 2022

Related U.S. Application Data

(60) Provisional application No. 62/815,475, filed on Mar. 8, 2019, provisional application No. 62/799,132, filed on Jan. 31, 2019.

(51) Int. Cl.
*A61B 17/62* (2006.01)
*A61B 17/66* (2006.01)

(52) U.S. Cl.
CPC .............. *A61B 17/62* (2013.01); *A61B 17/66* (2013.01)

(58) Field of Classification Search
CPC ................................. A61B 17/62; A61B 17/66
(Continued)

(56) References Cited

U.S. PATENT DOCUMENTS 8,864,750 B2    10/2014    Ross et al.
9,675,382 B2     6/2017    Bordeaux et al.
(Continued)

FOREIGN PATENT DOCUMENTS

EP          3011920 A1    4/2016
WO      2009105479 A1    8/2009
(Continued)

OTHER PUBLICATIONS

International Search Report and Written Opinion for International Application No. PCT/US2020/015558, dated Apr. 30, 2020.

*Primary Examiner* — Eduardo C Robert
*Assistant Examiner* — David C Comstock
(74) *Attorney, Agent, or Firm* — KDW Firm PLLC

(57) ABSTRACT

A strut measurement and feedback device and corresponding systems and methods for use with an external fixator are disclosed. The strut measurement and feedback device can be attached to a strut of an external fixator. The strut measurement and feedback device can confirm that the strut measurement and feedback device is attached to a proper strut to be adjusted. The strut measurement and feedback device can provide real-time feedback to an individual as the length of the strut is being adjusted to ensure the length adjustment complies with a prescription for the length of the (Continued)

strut. As a result, a patient can more effectively comply with the prescription as adjustments to the strut are made over time, thereby improving the likelihood of successful bone alignment.

31 Claims, 19 Drawing Sheets

(58) Field of Classification Search
USPC .............................................. 606/53, 56, 102
See application file for complete search history.

(56) References Cited

U.S. PATENT DOCUMENTS

| | | | |
|---|---|---|---|
| 10,082,384 B1* | 9/2018 | Singh | A61B 34/10 |
| 10,154,884 B2 | 12/2018 | Kumar et al. | |
| 2009/0206826 A1 | 8/2009 | Booth et al. | |
| 2013/0041288 A1* | 2/2013 | Taylor | A61B 5/6878 |
| | | | 600/587 |
| 2016/0022314 A1* | 1/2016 | Bordeaux | A61B 17/6416 |
| | | | 606/56 |
| 2016/0092651 A1 | 3/2016 | Austin et al. | |
| 2017/0071632 A1* | 3/2017 | Vikinsky | A61B 17/62 |
| 2017/0238967 A1 | 8/2017 | Bordeaux et al. | |
| 2017/0277859 A1 | 9/2017 | Burgherr et al. | |
| 2017/0354439 A1* | 12/2017 | Mannanal | A61B 17/62 |
| 2018/0228514 A1 | 8/2018 | Mannanal et al. | |
| 2019/0231259 A1* | 8/2019 | Cohen | G16H 40/63 |
| 2019/0336171 A1* | 11/2019 | Lavi | A61B 17/66 |
| 2020/0253640 A1* | 8/2020 | Mullaney | A61B 17/62 |
| 2021/0027879 A1* | 1/2021 | Noblett | A61B 17/66 |
| 2021/0307786 A1* | 10/2021 | Ross | A61B 5/0031 |

FOREIGN PATENT DOCUMENTS

| | | |
|---|---|---|
| WO | 2015136544 A1 | 9/2015 |
| WO | 2015164282 A1 | 10/2015 |

* cited by examiner

1400

```
┌─────────────────────────────────────────────────────────────┐
│   DETERMINE STRUT AND ATTACH MEASUREMENT DEVICE TO STRUT    │
│                            1402                             │
└─────────────────────────────────────────────────────────────┘
                              │
                              ▼
┌─────────────────────────────────────────────────────────────┐
│                DETECT ADJUSTMENT MADE TO STRUT              │
│                            1404                             │
└─────────────────────────────────────────────────────────────┘
                              │
                              ▼
┌─────────────────────────────────────────────────────────────┐
│             PROVIDE MEASUREMENT DATA TO USER DEVICE         │
│                            1406                             │
└─────────────────────────────────────────────────────────────┘
                              │
                              ▼
┌─────────────────────────────────────────────────────────────┐
│  COMPARE MEASUREMENT DATA TO PRESCRIPTION AND INDICATE      │
│                 RESULTS OF COMPARISON                       │
│                            1408                             │
└─────────────────────────────────────────────────────────────┘
                              │
                              ▼
┌─────────────────────────────────────────────────────────────┐
│ MAKE FURTHER ADJUSTMENTS TO STRUT BASED ON INDICATED        │
│              RESULTS OF COMPARISON                          │
│                            1410                             │
└─────────────────────────────────────────────────────────────┘
```

*FIG. 14*

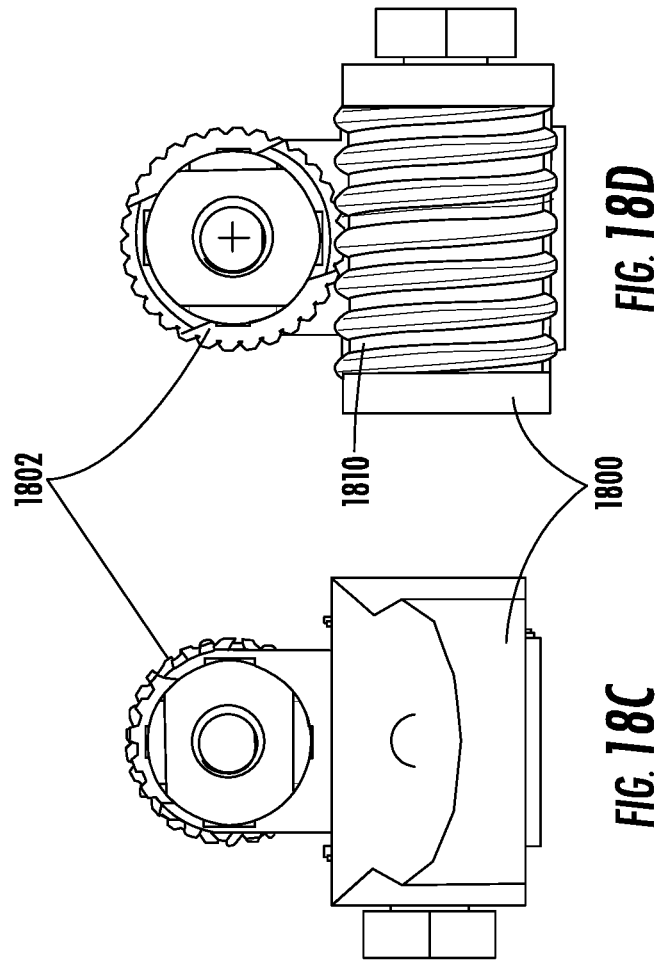
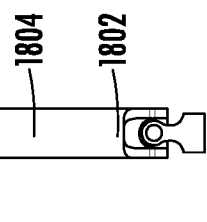
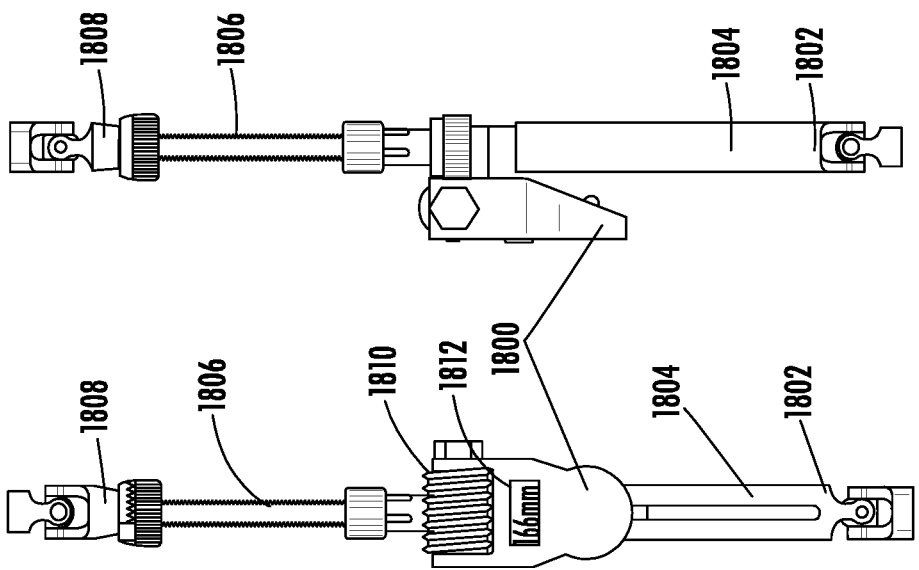

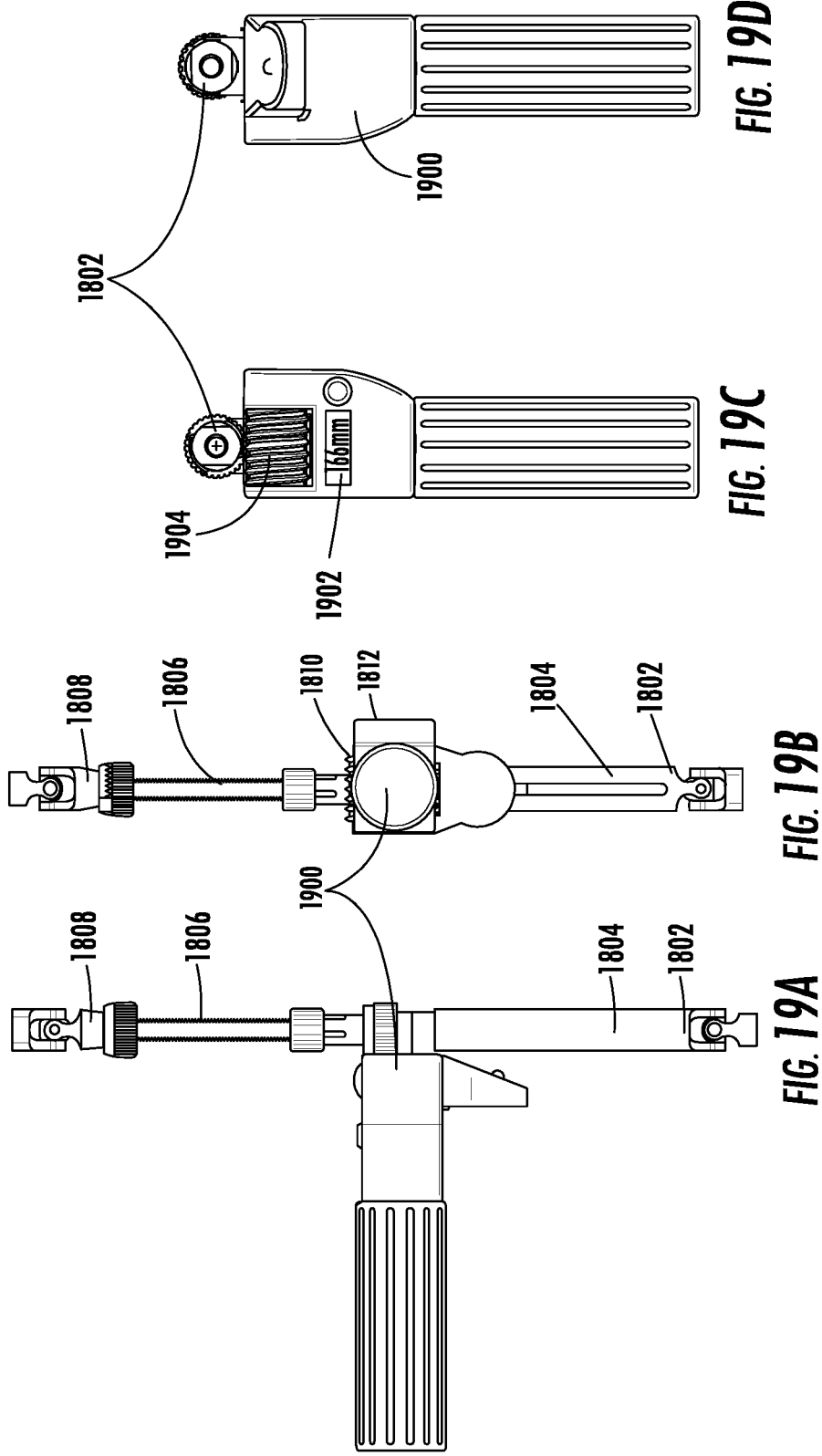

DEVICE FOR EXTERNAL FIXATION STRUT MEASUREMENT AND REAL-TIME FEEDBACK

CROSS-REFERENCE TO RELATED APPLICATIONS

The present application is a National Phase filing of International Application No. PCT/US2020/015558, filed Jan. 29, 2020, which is a non-provisional of, and claims the benefit of the filing date of, U.S. provisional patent application No. 62/799,132, filed on Jan. 31, 2019, entitled "Device for External Fixation Strut Measurement and Real-Time Feedback," and is a non-provisional of, and claims the benefit of the filing date of, U.S. provisional patent application No. 62/815,475, filed on Mar. 8, 2019, entitled "Device for External Fixation Strut Measurement and Real-Time Feedback," which are all hereby incorporated by reference into the present application in their entireties.

FIELD OF THE DISCLOSURE

The present disclosure relates generally to orthopedic devices, systems, and methods for facilitating fracture alignment, and particularly to a strut measurement device for use with an external fixator to provide real-time feedback on length adjustments to a strut to ensure the length adjustments are made in accordance with a predetermined prescription.

BACKGROUND OF THE DISCLOSURE

People suffer bone fractures each year. In many instances, a person that suffers a bone fracture is required to use a bone alignment device, or external fixator, to align two or more bones or pieces of bone. The bone alignment device often has multiple struts that are to be adjusted regularly (e.g., daily) in accordance with a prescription. The prescription specifies strut length adjustments to be made over time to ensure successful bone alignment.

Typically, the person suffering the bone fracture or a health care professional (HCP) adjusts the struts of the bone alignment device. It is often difficult for a patient or HCP to make the adjustments to each strut properly. That is, individuals often adjust the incorrect strut or adjust the strut to an incorrect length. Adjustments to the struts that do not comply with the prescription can cause significant setbacks to the care of the patient.

Thus, it would be beneficial to provide an easy to use apparatus, system, and method that confirms that adjustments to a strut of a bone alignment device are made properly. Additionally, it would be beneficial to provide real-time feedback to an individual adjusting a strut that indicates whether the correct strut is being adjusted and if the adjusted length is correct, in compliance with a given prescription. Further, it would be beneficial to provide the real-time adjustment feedback or resulting strut adjustments to a remote HCP, thereby allowing the remote HCP to more effectively monitor the progress of the patient.

SUMMARY OF THE DISCLOSURE

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

The present disclosure provides a strut measurement and feedback device. The strut measurement and feedback device can be attached to a strut of an external fixator. The strut measurement and feedback device can confirm that the strut measurement and feedback device is attached to a proper strut to be adjusted. The strut measurement and feedback device can determine if a length adjustment to the strut is correct. The strut measurement and feedback device can provide real-time feedback to an individual as the length of the strut is being adjusted to ensure the length adjustment complies with a prescription for the length of the strut. As a result, a patient can more effectively comply with the prescription as adjustments to the strut are made over time, thereby improving the likelihood of successful bone alignment.

In one embodiment, the strut measurement and feedback device can include a coupling component, a strut measurement component, and a communications interface. The coupling component enables the strut measurement and feedback device to be selectively attached and detached from a strut of an external fixator. The strut measurement component can determine which particular strut, the strut measurement and feedback device is attached to. The strut measurement component can also determine an absolute or relative positioning or length of a strut to which the strut measurement and feedback device is attached. The communications interface can provide measurement data and identification data regarding the strut to a user device to provide real-time feedback regarding adjustments to the length of the strut to an individual making the adjustments.

In one embodiment, the strut measurement component can include a camera for visualizing markings on the strut that can be used to determine the motion, position, or length of the strut.

In one embodiment, the strut measurement component can include a scanner for reading a barcode of the strut to identify the strut.

In one embodiment, the strut measurement component can include a radio-frequency identification (RFID) scanner for reading an RFID tag of the strut to identify the strut.

In one embodiment, the communications interface component can include a wireless communications interface for transmitting the measurement data and the identification data regarding the strut to the user device.

In one embodiment, the strut measurement and feedback device may include a device to adjust a length of the strut to which the strut measurement and feedback device is attached.

In one embodiment, the device for adjusting the length of the strut is configured to be removably attached to the strut measurement and feedback device.

In one embodiment, disclosed herein is a method for providing real-time feedback to an individual adjusting a strut of an external fixator using the strut measurement and feedback device, the method including attaching the strut measurement and feedback device to the strut, determining the strut to which the strut measurement and feedback device is attached, detecting an adjustment made to the strut including an initial length of the strut prior to adjustment, an ending length of the strut after the adjustment, and/or a measure of the change in length of the strut resulting from the adjustment, providing measurement data relating to the adjustment to a user device, comparing the adjustment to the strut to a predetermined prescription for adjusting the strut, and indicating to an individual implementing the adjustment whether or not the proper strut was adjusted or whether or not the adjusted length of the strut is correct.

In one embodiment, an external bone alignment device is disclosed. In use, the bone alignment device is arranged and configured to align two or more bones or pieces of bone. The bone alignment device comprising a first bone coupling device arranged and configured to engage a patient's first bone or piece of bone, a second bone coupling device arranged and configured to engage a patient's second bone or piece of bone, a plurality of struts coupled to the first and second bone coupling devices, each of the plurality of struts being arranged and configured to be lengthened and shortened so that adjustment of the strut moves the first bone coupling device relative to the second bone coupling device, and a strut measurement and feedback device arranged and configured to: (i) selectively attach to one of the plurality of struts and (ii) provide real-time information regarding an absolute or relative positioning or length of the strut to which the strut measurement and feedback device is attached.

In one embodiment, the strut measurement and feedback device includes a communication interface arranged and configured to communicate with a remote device to provide real-time feedback to an individual as the length of the strut to which the device is attached is being adjusted to ensure the length adjustment complies with a prescription for the length of the strut.

In one embodiment, the strut measurement and feedback device is arranged and configured to identify the strut to which it is attached from the plurality of struts.

In one embodiment, the strut measurement and feedback device can determine if a length adjustment to the strut to which it is attached is correct.

In one embodiment, the strut measurement and feedback device includes a coupling component arranged and configured to enable the strut measurement and feedback device to be selectively attached and detached from one of the plurality of struts, a strut measurement component for providing real-time information regarding an absolute or relative positioning or length of the strut to which the strut measurement and feedback device is attached, and a communications interface arranged and configured to provide measurement data to a user device to provide real-time feedback regarding adjustments to the length of the strut to an individual making the adjustments.

In one embodiment, the strut measurement component is also arranged and configured to determine the strut, from the plurality of struts, to which the strut measurement and feedback device is attached.

In one embodiment, the communications interface is also arranged and configured to provide identification data regarding the strut to a user device to provide real-time feedback regarding adjustments to the length of the strut to which the strut measurement and feedback device is attached.

In one embodiment, the strut measurement component is a camera arranged and configured to read visualizing markings positioned on the strut to which the strut measurement and feedback device is attached, the visualizing markings determining a length of the strut.

In one embodiment, the strut measurement component is a scanner for reading a barcode positioned on the strut to which the strut measurement and feedback device is attached, the barcode identifying the strut to which the strut measurement and feedback device is attached.

In one embodiment, the strut measurement component includes a radio-frequency identification (RFID) scanner for reading an RFID tag positioned on the strut to which the strut measurement and feedback device is attached, the RFID tag identifying the strut to which the strut measurement and feedback device is attached.

In one embodiment, the communications interface component includes a wireless communications interface for transmitting measurement data and identification data regarding the strut to which the strut measurement and feedback device is attached to the user device.

In one embodiment, the strut measurement and feedback device includes a device to adjust a length of the strut to which the strut measurement and feedback device is attached.

In one embodiment, the device to adjust the length of the strut is arranged and configured to be removably attached to the strut measurement and feedback device.

In one embodiment, the strut measurement and feedback device is arranged and configured to detect an adjustment made to the strut to which the strut measurement and feedback device is attached, the adjustment information including one of providing an initial length of the strut prior to adjustment and an ending length of the strut after the adjustment, and a measure of the change in length of the strut resulting from the adjustment.

In one embodiment, the external bone alignment device further comprises the user device arranged and configured to compare the adjustment to the strut to a predetermined prescription for adjusting the strut and indicating to an individual implementing the adjustment whether or not the proper strut was adjusted or whether or not the adjusted length of the strut is correct.

In one embodiment, a device to measure and provide feedback associated with an external bone alignment device is also disclosed. The device comprises a coupling component arranged and configured to selectively attach to one of a plurality of struts of the external bone alignment device, the external bone alignment device arranged and configured to align two or more bones or pieces of bone, the external bone alignment device comprising a first bone coupling device arranged and configured to engage a patient's first bone or piece of bone, a second bone coupling device arranged and configured to engage a patient's second bone or piece of bone, the plurality of struts coupled to the first and second bone coupling devices, each of the plurality of struts being arranged and configured to be lengthened and shortened so that adjustment of the strut moves the first bone coupling device relative to the second bone coupling device; and circuitry to provide real-time information regarding an absolute or relative positioning or length of the strut to which the strut measurement and feedback device is attached.

In one embodiment, the circuitry includes a communication interface arranged and configured to communicate with a remote device to provide real-time feedback to an individual as the length of the strut to which the device is attached is being adjusted to ensure the length adjustment complies with a prescription for the length of the strut.

In one embodiment, the circuitry is arranged and configured to identify the strut to which it is attached from the plurality of telescopic struts.

In one embodiment, the circuitry can determine if a length adjustment to the strut to which it is attached is correct.

In one embodiment, the circuitry includes the coupling component arranged and configured to enable the strut measurement and feedback device to be selectively attached and detached from one of the plurality of struts, a strut measurement component for providing real-time information regarding an absolute or relative positioning or length of the strut to which the strut measurement and feedback device is attached, and a communications interface arranged and configured to provide measurement data to a user device to provide real-time feedback regarding adjustments to the length of the strut to an individual making the adjustments.

In one embodiment, the strut measurement component is also arranged and configured to determine the strut, from the plurality of struts, to which the circuitry is attached.

In one embodiment, the communications interface is also arranged and configured to provide identification data regarding the strut to a user device to provide real-time feedback regarding adjustments to the length of the strut to which the circuitry is attached.

In one embodiment, the strut measurement component is a camera arranged and configured to read visualizing markings positioned on the strut to which the circuitry is attached, the visualizing markings determining a length of the strut.

In one embodiment, the strut measurement component is a scanner for reading a barcode positioned on the strut to which the circuitry is attached, the barcode identifying the strut to which the circuitry is attached.

In one embodiment, the strut measurement component includes a radio-frequency identification (RFID) scanner for reading an RFID tag positioned on the strut to which the circuitry is attached, the RFID tag identifying the strut to which the circuitry is attached.

In one embodiment, the communications interface component includes a wireless communications interface for transmitting measurement data and identification data regarding the strut to which the circuitry is attached to the user device.

In one embodiment, the circuitry includes a device to adjust a length of the strut to which the circuitry is attached.

In one embodiment, the device to adjust the length of the strut is arranged and configured to be removably attached to the circuitry.

In one embodiment, the circuitry is arranged and configured to detect an adjustment made to the strut to which the circuitry is attached, the adjustment information including one of providing an initial length of the strut prior to adjustment and an ending length of the strut after the adjustment, and a measure of the change in length of the strut resulting from the adjustment.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

By way of example, a specific embodiment of the disclosed device will now be described, with reference to the accompanying drawings, in which:

FIG. 14 illustrates a logic flow associated with the compliance monitoring system of FIG. 2 according to one embodiment;

FIG. 18A illustrates a front view of a ninth embodiment of the strut measurement and feedback device depicted in FIGS. 2 and 3;

FIG. 18B illustrates a side view of the embodiment of the strut measurement and feedback device depicted in FIG. 18A;

FIG. 18C illustrates a bottom view of the embodiment of the strut measurement and feedback device depicted in FIG. 18A;

FIG. 18D illustrates a top view of the embodiment of the strut measurement and feedback device depicted in FIG. 18A;

FIG. 19A illustrates a side view of a tenth embodiment of the strut measurement and feedback device depicted in FIGS. 2 and 3;

FIG. 19B illustrates a front view of the embodiment of the strut measurement and feedback device depicted in FIG. 19A;

FIG. 19C illustrates a top view of the embodiment of the strut measurement and feedback device depicted in FIG. 19A; and FIG. 19D illustrates a bottom view of the embodiment of the strut measurement and feedback device depicted in FIG. 19A.

Figure 1:
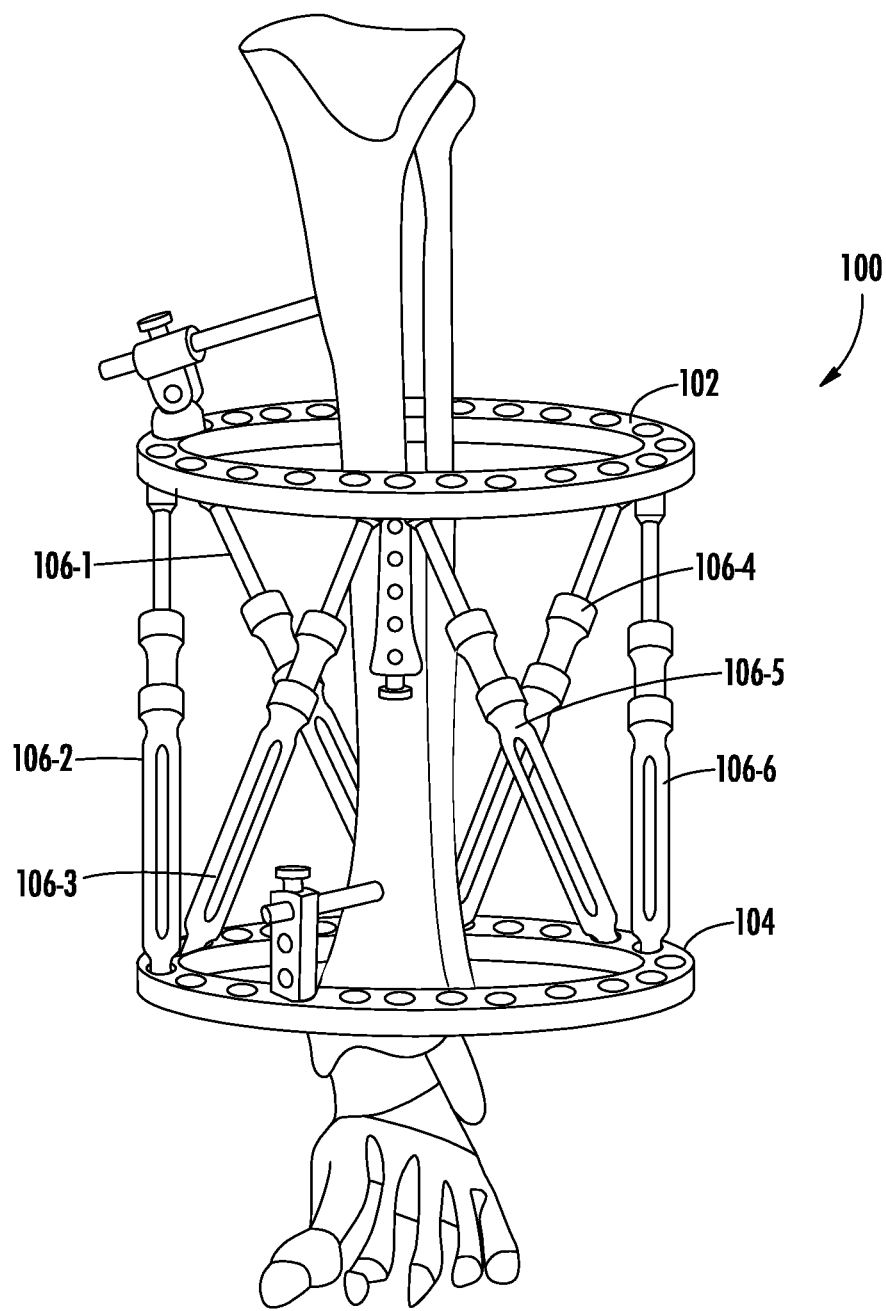
FIG. 1 illustrates an embodiment of a bone alignment device.

The drawings are not necessarily to scale. The drawings are merely representations, not intended to portray specific parameters of the disclosure. The drawings are intended to depict various embodiments of the disclosure, and therefore are not be considered as limiting in scope. In the drawings, like numbering represents like elements.

DETAILED DESCRIPTION

Devices, systems, and methods for providing real-time feedback on the length of a strut of an external fixator are provided. The real-time feedback can ensure that the length of each strut is adjusted correctly in compliance with a predetermined prescription for facilitating fracture alignment. The real-time feedback can be provided by a device that can attach to a strut and wirelessly transmit linear distance measurements to, for example, a user device. Indications as to whether the adjusted length of the strut are correct can be presented to an individual in real-time while the individual is adjusting the strut length. Once the correct strut length is reached, the device can be detached and attached to a next strut of the external fixator. In this manner, each strut of the external fixator can be adjusted to the proper length, in compliance with the predetermined prescription. Further, the device can identify each strut which is being adjusted. Additionally, measurement data for each strut can be stored and provided to a remote health care provider (HCP) to provide the HCP with more detailed information regarding progress of the patient and conformance to the predetermined prescription.

FIG. 1 illustrates an embodiment of a bone alignment device 100. The bone alignment device 100 can be an external fixator. The bone alignment device 100 can include a first bone coupling mechanism, member, device, etc., a second bone coupling mechanism, member, device, etc., and a plurality of interconnected telescopic struts. For example, as shown in FIG. 1, in one embodiment, the bone alignment device 100 can form a hexapod having a circular, metal frame with a first ring 102 and a second ring 104 connected by six telescopic struts 106 (labeled as struts 106-1 through 106-6 in FIG. 1). Each strut 106 can be independently lengthened or shortened relative to the rest of the frame, thereby allowing for six different axes of movement.

In one embodiment, each strut 106 may include an outer body component and an inner rod component (e.g., a threaded rod). To lengthen or shorten one of struts 106, the outer body component and the inner rod component can be moved or translated relative to one another. Thus arranged, each strut may be in the form of a telescopic device. Often a strut pin coupled to the inner rod component can be visualized within a slot or opening formed in the outer body component to determine the relative movement of the inner rod component relative to the outer body component. For example, as the inner rod component is translated relative to the outer body component, the strut pin moves in unison with the inner rod component within the slot of the outer body component.

As will be described herein, the features according to the present disclosure may be used with any suitable bone alignment device now known or hereafter developed. In this regard, the present disclosure should not be limited to the details of the bone alignment device and/or struts disclosed and illustrated herein unless specifically claimed and that any suitable bone alignment device can be used in connection with the principles of the present disclosure.

The bone alignment device 100 can be used to treat a variety of skeletal fractures of a patient. Typically, the bone alignment device 100 is positioned around the patient and is used to align two or more bones or pieces of bone. To do so, a length of each strut 106 can be incrementally adjusted (e.g., shortened or lengthened) in accordance with a prescription that specifies adjustments to be made to each strut 106 over time to ensure successful bone alignment. In many instances, the length of each strut 106 should be adjusted daily to comply with the provided prescription. As such, in use, a prescription may, for example, designate a specific amount of adjustment that needs to be made to each strut on, for example, a daily basis. In use, each strut may be adjusted daily by a varying amount.

The adjustments to the struts 106 are usually made by either the patient or a caregiver. To make an adjustment, an individual can refer to a graduated scale that is laser etched onto each strut 106. The scale, however, can be difficult for the individual making the adjustments to observe when the bone alignment device 100 is positioned on the patient. The individual making the adjustment may also rely on a tactile "click" that can be felt by the patient when the length of the strut 106 is adjusted by a fixed amount (e.g., 1 mm). The tactile click, however, does not indicate the direction in which the strut 106 was adjusted. In addition, individuals may often adjust the incorrect strut (e.g., on a daily basis, each strut may need to be adjusted a different amount, the individual may inadvertently adjust the wrong strut, or adjust the correct strut by an incorrect amount). Furthermore, an individual may inadvertently rotate one or more struts in the wrong direction thereby, for example, shortening a strut instead of lengthening the strut. Thus, despite implementing safeguards such as, for example, the inclusion of the scale and the tactile click, it may be difficult for individuals to confirm that the proper length of the strut 106 was reached as specified by the prescription when an adjustment to the strut 106 is made. As a result, it is common for individuals to not comply with the prescription when an adjustment is made.

A patient generally has follow-up clinical visits, for example, a patient may have a clinical visit every two weeks, so that the patient's clinician can evaluate the patient's progress and modify the bone alignment device 100 or related prescription as necessary. Incorrect adjustments to the struts 106 that can occur between clinical visits can result in significant deviations in the correction path of the bone fragments compared to what was prescribed, thereby causing significant setbacks in the treatment of the patient.

Figure 2:
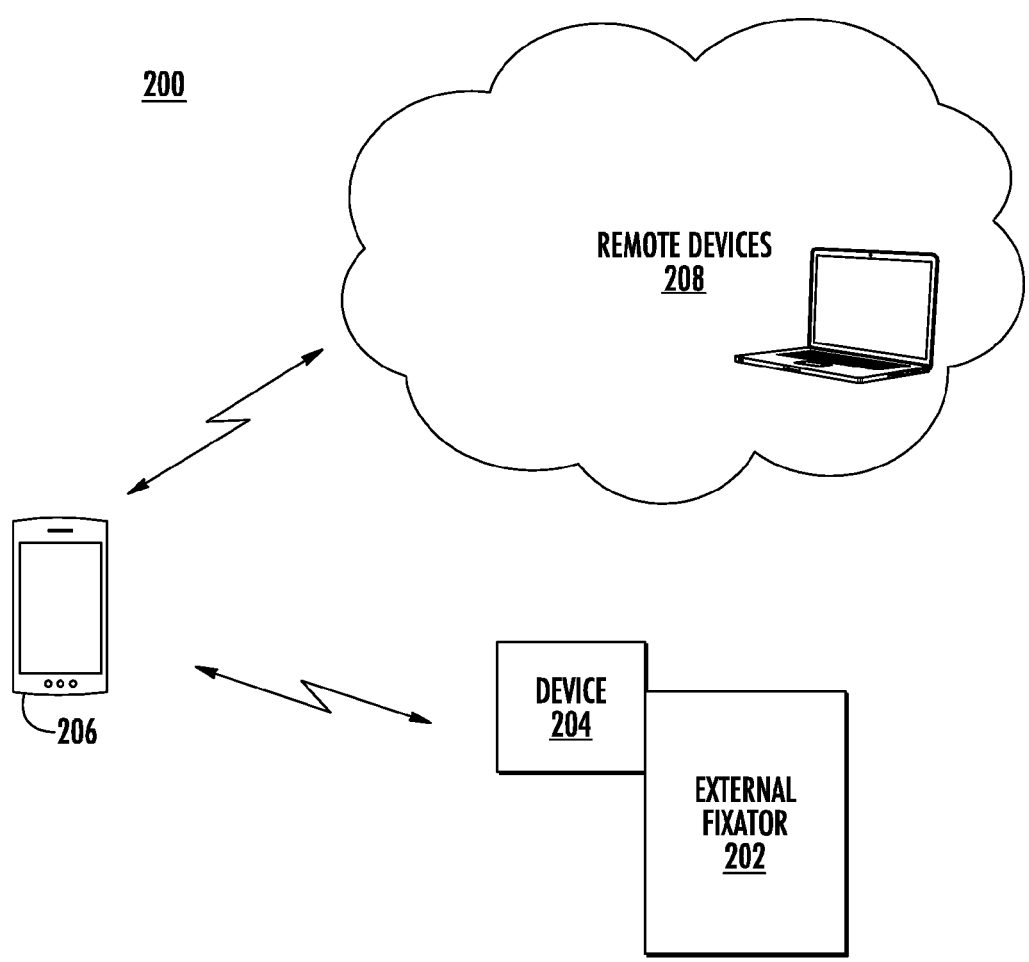
FIG. 2 illustrates an embodiment of a compliance monitoring system in accordance with one aspect of the present disclosure.

FIG. 2 illustrates an embodiment of a compliance monitoring system 200 that can be used to monitor strut compliance in connection with an external fixation system. The compliance monitoring system 200 can include an external fixator 202, a strut measurement and feedback device 204, and a user device 206. In various embodiments, the external fixator 202 can be the bone alignment device 100 depicted in FIG. 1. Alternatively, the external fixator 202 can be any other bone alignment device now known or hereafter developed.

In use, the strut measurement and feedback device 204 can be selectively coupled to each strut of the external fixator 202. In one embodiment, the strut measurement and feedback device 204 can be coupled to each strut one at a time. In use, in one embodiment, the strut measurement and feedback device 204 can determine which strut the strut measurement and feedback device 204 is coupled to and can provide real-time feedback as to the position of each strut (e.g., can determine absolute position of each strut, which can then be used to determine the change in length which the strut undergoes by, for example, comparing the start position to the finish position). The real-time feedback can be provided to the user device 206 to enable a patient, a caregiver, a health care professional (HCP), or whoever is making the adjustments to verify that adjustments to the struts of the external fixator 202 are being properly made in compliance with a predetermined prescription.

That is, as will be described in greater detail herein, in use, the strut measurement and feedback device 204 can take on any of a number of different forms. The strut measurement and feedback device 204 can perform one or more of the following features, among others: collect data, process data, transmit data, receive data and/or provide feedback. For example, in some embodiments, the strut measurement and feedback device 204 can perform all of these features. Alternatively, in some embodiments, the strut measurement and feedback device 204 can collect data and transmit data to, for example, the user device 206, which can process the data and/or provide feedback. Thus arranged, in use, the strut measurement and feedback device 204, either alone or in combination with, the user device 206, can determine/detect what specific strut the strut measurement and feedback device 204 is coupled to (e.g., strut 106-1 or 106-2, 106-3, etc.), determine if it is attached properly to the strut (e.g., indicate if the strut measurement and feedback device 204 is correctly or incorrectly attached to the strut), detect the initial position of the strut (e.g., initial length of strut), detect the adjusted position of the strut (e.g., adjusted length of the strut), and/or determine change in length of the strut, transmit data to, for example, the user device 206, receive data (e.g., the prescription) from, for example, the user device 206, store a patient's prescription for adjusting the position of the various struts, compare data including the adjusted length or the adjusted position of the strut to the prescription, check for compliance with the prescription, provide feedback or indication of compliance and/or non-compliance, etc.

In use, after coupling the strut measurement and feedback device 204 to a strut in the external fixator 202, the strut measurement and feedback device 204 determines (e.g., measures) changes to the length of the strut of the external fixator 202. That is, in use, the strut measurement and feedback device 204 can measure and/or monitor a position of a strut to which it is coupled (e.g., can measure or monitor an absolute or relative position of the inner rod component relative to the outer rod component). In addition, the strut measurement and feedback device 204, either alone or in combination with the user device 206, can indicate if the adjustment is being made to the correct strut, can indicate if the direction of adjustment is proper, and/or can indicate if the adjusted length complies with the predetermined prescription.

The strut measurement and feedback device 204 can communicate directly or indirectly with the user device 206. The user device 206 may be any suitable user device now known or hereafter developed including, for example, an electronic device and/or a computing device such as, for example, a smartphone, a tablet, a laptop, a notebook, a netbook, a personal computer (PC), etc. In various embodiments, the strut measurement and feedback device 204 and the user device 206 can communicate over any known wireless communication standard or protocol. Example wireless connections and/or protocols may include, for example, Wi-Fi (e.g., any IEEE 802.11 a/b/g/n network), Bluetooth, Bluetooth Low Energy (BLE), Near-Field Communication (NFC), any cellular communication standard, any infrared communication protocol, etc.

The communication connectivity between the strut measurement and feedback device 204 and the user device 206 enables data or information such as, for example, measurement data, strut identification data, compliance data, etc. determined by the strut measurement and feedback device 204 to be provided to the user device 206 for review by the patient or HCP. Accordingly, as adjustments are made to each strut of the external fixator 202, the user device 206 can present real-time measurement and/or compliance data determined by the strut measurement and feedback device 204. As a result, the patient or HCP can more easily determine if adjustments are being properly made (e.g., direction and amount of displacement) and if adjustments are being made to the proper strut.

As further shown in FIG. 2, the user device 206 can communicate directly or indirectly with one or more remote computing devices, remote computer networks, and/or remote cloud networks or platforms 208 (collectively referred to as "remote devices 208" without intent to be limiting). The real-time data including, for example, the measurement data, monitoring data, etc. provided by the strut measurement and feedback device 204 to the user device 206 can be relayed to the remote devices 208. This enables a remote HCP to monitor in real-time the patient's compliance with the predetermined prescription. In an embodiment, real-time measurement and/or compliance data determined by the strut measurement and feedback device 204 can be provided to one or more remote devices 208 after an adjustment to a strut of the external fixator 202 has been made or after adjustments to all struts have been made. Alternatively, real-time measurement and/or compliance data determined by the strut measurement and feedback device 204 can be provided to one or more remote devices 208 in real-time (e.g., as adjustments to any strut are being made), thereby allowing a remote HCP to directly interact with the individual making the adjustments through communications with the user device 206.

In various embodiments, the user device 206 can include software or an application (e.g., an "app") that receives real-time data (e.g., measurement data, compliance data, etc.) determined by the strut measurement and feedback device 204. The app on the user device 206 can provide feedback to the individual adjusting the external fixator 202 as adjustments are made. The feedback can be any feedback include, for example, visual, tactile, and/or audible feedback. The feedback provided through the user device 206 based on real-time measurement and/or compliance data determined by the strut measurement and feedback device 204 can increase a likelihood that adjustments to the external fixator are made properly and/or comply with a prescription. In various embodiments, the user device 206, including the capabilities, features, and/or functionality of the user device 206, as well as the capabilities, features, and/or functionality of any software or app provided on the user device 206, can be as described in U.S. patent application Ser. No. 14/891,540, filed May 14, 2014, which is hereby incorporated by reference in its entirety.

The prescription for movement of the struts of the external fixator 202 can be stored remotely (e.g., on one or more remote devices 208) and/or can be stored on the user device 206. The real-time measurement and/or compliance data determined by the strut measurement and feedback device 204 can be compared to the stored prescription either locally or remotely to provide feedback to the individual adjusting the struts of the external fixator 202. Accordingly, the feedback provided to the individual adjusting the external fixator 202 can originate remotely (e.g., by one or more remote device 208) and can be transmitted to the user device 206 or can originate locally (e.g., by the app running on the user device 206).

The communication connectivity between the patient, the individual adjusting the external fixator 202, and a remote HCP by the compliance monitoring system 200 enables additional data or information to be shared. In various embodiments, visual, textual, and/or voice data or other information can be shared between the user device 206 and a remote computing device 208. In this way, the patient, HCP, and/or other individual adjusting the external fixator 202 can communicate with a remote HCP or other individual as adjustments are being made or at any other time. In various embodiments, the patient coupled to the external fixator 202 can transmit information related to pain or any other discomforts to the remote HCP. In various embodiments, the remote HCP can modify the prescription for the use of the external fixator 202 and can transmit it to the user device 206 for storage and/or use.

The strut measurement and feedback device 204 may be any suitable device now known or hereafter developed that can be attached and detached from a strut of the external fixator 202, that can determine an absolute and/or relative positioning the strut (e.g., determine adjusted length of a strut by, for example, comparing a start position versus a finish position), and can provide data or other information regarding the adjusted length, and/or absolute and/or relative positioning of the strut as adjustments to the strut are being made. In this way, the patient and/or HCP adjusting the external fixator 202 can properly adjust the struts, thereby improving the care provided to the patient and ensuring compliance with a predetermined prescription for adjusting the external fixator 202. Further, a remote HCP can monitor treatment progress remotely based on connectivity between the user device 208 and the one or more remote devices 208. In addition, as will be described herein, the strut measurement component or module 304 can also determine which particular strut the strut measurement and feedback device 204 is attached.

Various embodiments, features, and/or capabilities of the strut measurement and feedback device 204 are described below. In various embodiments, as described herein, the strut measurement and feedback device 204 can include components to visualize markings (e.g., a scale) provided on a strut of the external fixator 202. By visualizing the markings provided on the strut, the strut measurement and feedback device 204 can determine an absolute position of the strut as adjustments to the strut are made.

In various other embodiments, as described herein, the strut measurement and feedback device 204 can include components to measure a distance from a fixed point on a strut body to either the bottom of a rod positioned within the strut or to a pin positioned within a slot of the strut. Because each strut of the external fixator 202 can have different lengths, the measured distance can be the same for two struts having different overall lengths. Accordingly, the strut measurement and feedback device 204 can further determine the strut on which it is attached. By knowing the strut to which it is attached, the strut measurement and feedback device 204 and/or the user device 206 can determine an accurate measure of an adjusted length for the strut based on the aforementioned measured distance. Information regarding the length of each strut of the external fixator 202 can be stored and/or accessible to the strut measurement and feedback device 204 and/or the user device 206 for making an accurate determination of the length of a strut (e.g., a true or absolute strut length).

Figure 3:
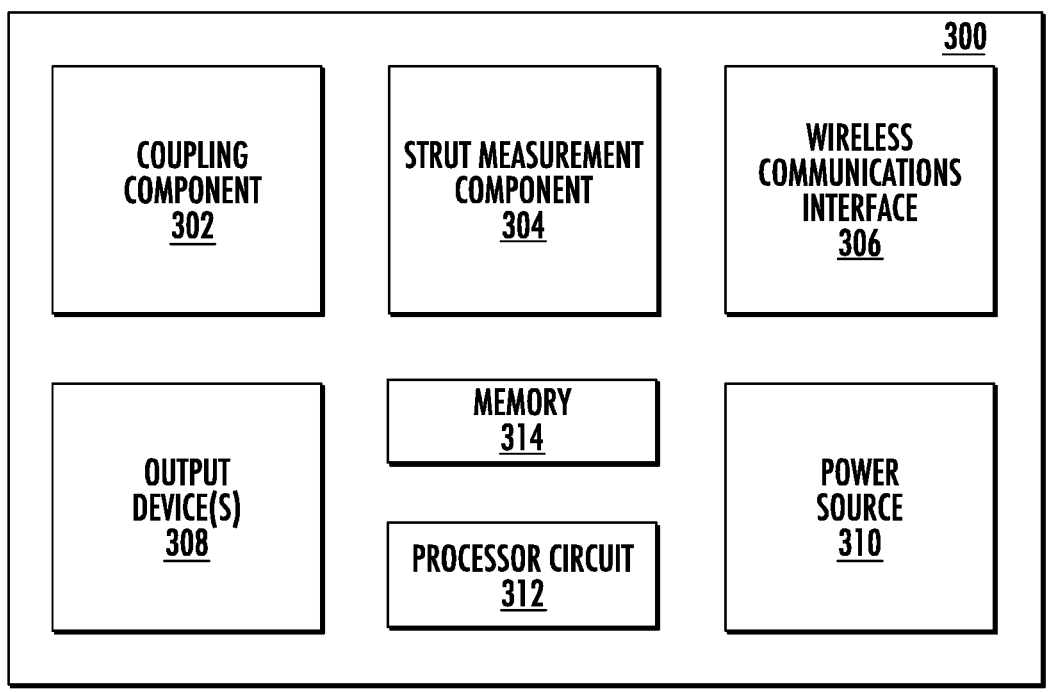
FIG. 3 illustrates a block diagram of an embodiment of a strut measurement and feedback device depicted in FIG. 2.

FIG. 3 illustrates an embodiment of the strut measurement and feedback device 204. Specifically, FIG. 3 provides a block diagram of circuitry 300 to interconnect functional components of the strut measurement and feedback device 204. As shown, the strut measurement and feedback device 204 may include a coupling component or module 302 for selectively coupling and detaching the strut measurement and feedback device 204 to and from the strut. The coupling component 302 can provide one or more mechanisms for coupling and decoupling the strut measurement and feedback device 204 to a strut of the external fixator 202. The coupling component 302 can include one or more mechanical components, electrical components, electromechanical components, or any combination thereof.

The strut measurement and feedback device 204 may include a strut measurement component or module 304. The strut measurement component 304 enables the strut measurement and feedback device 204 to determine an absolute and/or a relative positioning of a strut to which the strut measurement and feedback device 204 is coupled. The strut measurement component or module 304 can also determine to which particular strut the strut measurement and feedback device 204 is attached. The strut measurement component can include one or more mechanical components, electrical components, electromechanical components, or any combination thereof.

The strut measurement and feedback device 204 may include a wireless communications interface 306. The wireless communications interface 306 may provide interfaces for communicating with any local or remote device or network through any wireless communication technology. The wireless communications interface 306 enables the strut measurement and feedback device 204 to wirelessly transmit and receive data or information with the user device 206 and/or one or more remote computing devices 208 either directly or indirectly.

The strut measurement and feedback device 204 may include one or more output devices or components 308. The output devices 308 can provide visual, audible, and/or tactile feedback to the user of the strut measurement and feedback device 204. In various embodiments, the output device 308 can include one or more speakers, one or more light emitting diodes (LEDs), and/or a display (e.g., a touchscreen). The output devices 308 can indicate to the user of the strut measurement and feedback device 204 whether or not the strut measurement and feedback device 204 is being used properly (e.g., if the strut measurement and feedback device 204 is attached properly or improperly) and/or can indicate whether a strut measurement is in progress, is complete, and/or was done incorrectly or erroneously.

The strut measurement and feedback device 204 may include a power source 310. The power source 310 may include electrical power connections and/or a battery. The power source 310 may provide power to any of the constituent functional components of the strut measurement and feedback device 204 depicted in FIG. 3. In various embodiments the power source can be a rechargeable battery or, alternatively, a replaceable battery.

The strut measurement and feedback device 204 may further include a processor circuit 312 and an associated memory component 314. The memory component 314 may store one or more programs for execution by the processor circuit 312 to implement one or more functions or features of the strut measurement and feedback device 204 as described herein. The processor circuit 312 may be implemented using any processor or logic device. The memory component 314 can be implemented using any machine-readable or computer-readable media capable of storing data, including both volatile and non-volatile memory.

The processor circuit 312 may implement the functionalities of any of the components depicted in FIG. 3 or may control or adjust operation of any of the depicted components. Each component depicted in FIG. 3 may be coupled to the processor circuit 312 as well as any other depicted component. For instance, the processor circuit 312 may, in some embodiments, determine a strut identifier (ID) from a strut and store the strut ID in memory 314, compare the strut ID with a strut ID associated with an adjustment to determine if the strut measurement and feedback device 204 is coupled with the correct strut to perform the adjustment. In further embodiments, the processor circuit 312 may, in some embodiments, compare a strut adjustment performed on the external fixator 202 (also referred to as a bone alignment device or external bone alignment device) with a prescribed adjustment for the same strut ID in the memory 314 to determine if the strut adjustment matches the prescribed adjustment. In several embodiments, the processor circuit 312 may communicate with the wireless communications interface 306 and/or the output device(s) 308 to provide real-time feedback to a remote individual and/or an individual performing the adjustments to the struts of the external fixator 202. The depicted components may be implemented in hardware or software as appropriate, or any combination thereof.

Various embodiments of the strut measurement and feedback device 204 are described herein. The various embodiments may vary by shape, size, and/or form factor. The various embodiments may vary by implementation of the constituent components described in relation to FIG. 3. Features and/or functionalities of any described embodiment can be combined or used in combination with features and/or functionalities of any other embodiment described herein as will be appreciated by one skilled in the relevant arts.

Figure 4:
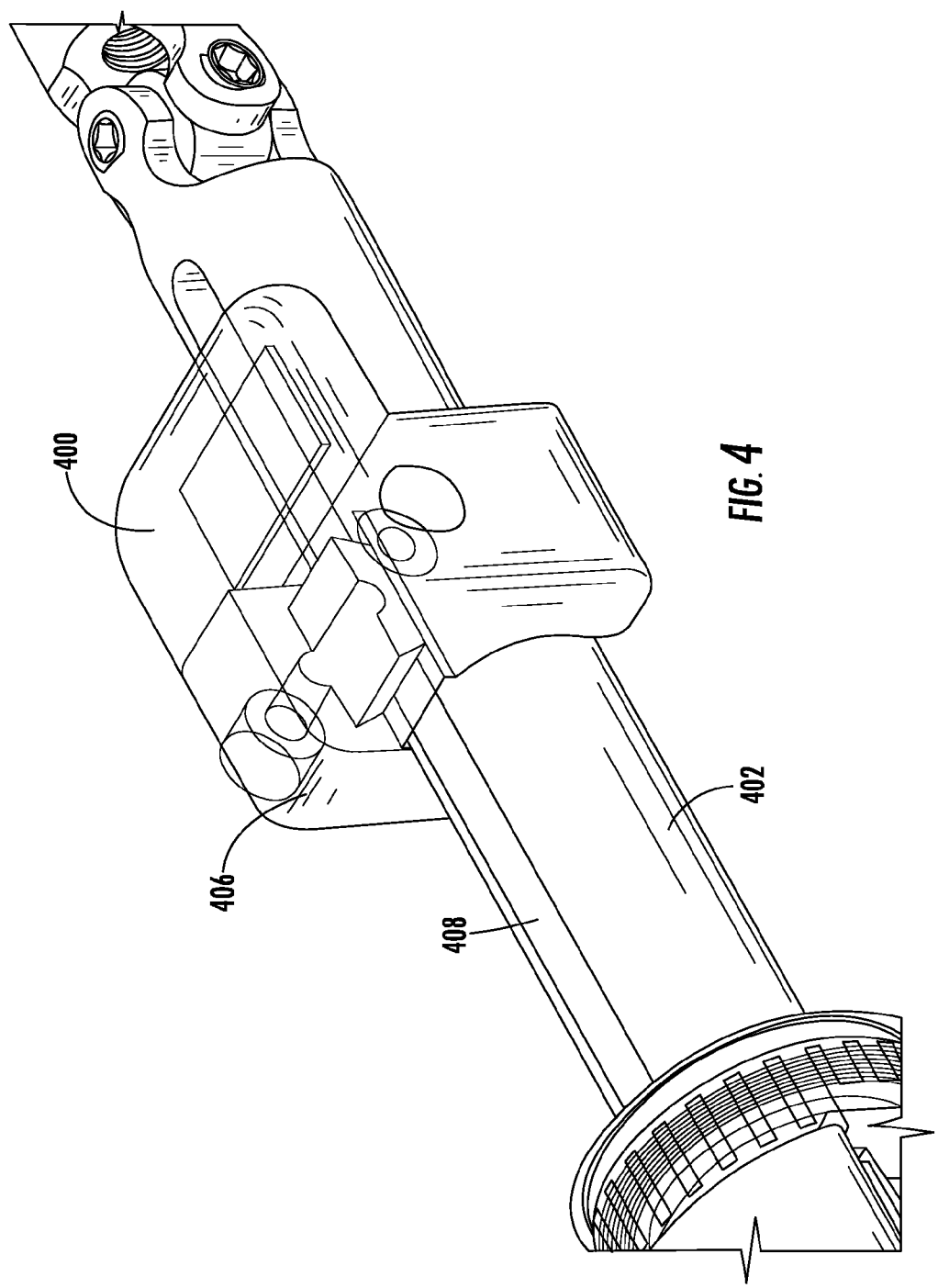
FIG. 4 illustrates a first embodiment of the strut measurement and feedback device depicted in FIGS. 2 and 3.

FIG. 4 illustrates a first embodiment of a strut measurement and feedback device 400. The strut measurement and feedback device 400 may represent the strut measurement and feedback device 204 as depicted in FIGS. 2 and 3. As shown in FIG. 4, the strut measurement and feedback device 400 is coupled to a strut 402. The strut 402 can be a strut of the external fixator 202 as depicted in FIG. 2.

The strut measurement and feedback device 400 may include a high-resolution camera 406. The camera 406 may be used to visualize laser markings (not shown in FIG. 4 for simplicity) on the outside of the strut 402. The camera 406 may also be used to visualize movement of a strut pin (not shown in FIG. 4 for simplicity) positioned within a slot 408 of the strut 402. Multiple images of the strut pin can be captured and analyzed to calculate the motion of the strut pin within the slot 408. In various embodiments, the motion of the strut pin can be analyzed using image processing functionality residing on the strut measurement and feedback device 400 (e.g., image processing software stored on the strut measurement and feedback device 400). In various embodiments, the motion of the strut pin can be analyzed using image processing functionality residing on the user device 206 (e.g., image processing software stored on the user device 206).

Image processing capabilities residing on the user device 206 and/or the strut measurement and feedback device 400 may be used to "read" a strut length from laser markings on the body of the strut 402 using Optical Character Recognition (OCR) or similar image processing capability. In this way, a measurement of the length of the strut 402 may be "absolute," enabling the user device 206 and/or the strut measurement and feedback device 400 to determine the starting length and the ending length of any strut to which the strut measurement and feedback device 400 is attached by analyzing multiple images of the laser markings as the strut is moved.

In various embodiments, the strut 402 can include a unique marking pattern that could be recognized by the camera 406. The marking pattern can be any type of pattern including, for example, a dot matrix pattern. The marking pattern may allow for enhanced resolution and accuracy, as the markings for the camera 406 would not have to be human readable.

In various embodiments, the strut measurement and feedback device 400 can have a shape and/or a form factor that allows the strut measurement and feedback device 400 to snap over an outer diameter of the strut 402 while allowing the strut measurement and feedback device 400 to slide along the strut 402. As shown in FIG. 4, the strut measurement and feedback device 400 can resemble a C-Clip housing but is not so limited.

In a first additional embodiment, a user can slide the strut measurement and feedback device 400 along the strut 402 in any direction until the camera 406 is positioned over the strut pin in the slot 408. When the camera 406 is positioned over the strut pin, any combination of visual and/or audible signals can be provided by the strut measurement and feedback device 400 to indicate to the user that the strut measurement and feedback device 400 is properly positioned.

In a second additional embodiment, the strut pin can be made to protrude out of the slot 408. The strut measurement and feedback device 400 can then be moved by the user along the strut 402 until the strut measurement and feedback device 400 contacts the protruding strut pin.

In a third additional embodiment, the strut measurement and feedback device 400 can be coupled or connected to the strut pin such that the strut measurement and feedback device 400 translates along the strut 402 as the length of the strut 402 is changed. In each of the aforementioned embodiments, the strut measurement and feedback device 400 can be properly positioned and then left in place while adjustments to the length of the strut 402 are made. An accurate measurement of the absolute length of the strut 402 can then be made as the strut pin movement reflects the movement and therefore length of the strut 402.

In various embodiments, the strut measurement and feedback device 400 can provide a measurement of an absolute length of the strut 402 when not coupled to the strut pin. Under such scenarios, the camera 406 may be provided with a minimum field of view sufficiently large to visualize the strut pin and identifiable laser marking located on the struts. In various embodiments, when the camera 406 includes a wide-angle lens, then the camera 406 may be able to visualize an entire length of the slot 408. In various embodiments, when the camera 406 includes a wide-angle lens, then the strut measurement and feedback device 400 may be coupled to the strut 402 at a fixed location. For example, the strut measurement and feedback device 400 could be attached to a midpoint of the strut 402 and may not be movable along the length of the strut 402. Alternatively, the strut measurement and feedback device 400 could be attached adjacent to one end of the strut 402.

As described herein, as the strut measurement and feedback device 400 collects data related to the length of the strut 402 as adjustments are made to the strut 402, the strut measurement and feedback device 400 can provide the collected measurement data to the user device 206 in real-time. The measurement data relating to the strut 402 can then be provided to user of the user device 206 in a user-facing app to allow the user to view the real-time length of the strut 402 length as adjustments are made. In various embodiments, the app can notify the user when the length of the strut 402 matches a prescribed strut length for the strut 402. In various embodiments, the app can also provide feedback to indicate when an adjustment has overshot the prescribed length for the strut 402 and/or when an adjustment has been made in an improper direction.

The app can provide indications through one or more output devices of the user device 206. As an example, the app can provide feedback through any combination of visual, audible, or haptic feedback through the user device 206. Additionally, real-time data regarding the length of the strut 402 can be provided to a remote HCP through the one or more remote devices 208. This allows a remote HCP of a patient the ability to assess patient compliance (e.g., in relation to the predetermined prescription) by monitoring the arrangement and position of the external fixator 202.

In various embodiments, the strut measurement and feedback device 400 can automatically identify each strut of the external fixator 202. In one embodiment, each strut of the external fixator 202 can include a color-coded identification (ID) band that the strut measurement and feedback device 400 can identify as a unique strut ID based on color recognition (e.g., using a color detection sensor). In a second embodiment, an ID band on each strut of the external fixator 202 can include an NFC device, such as a radio-frequency identification (RFID) tag, to identify a unique strut ID for each strut. The strut measurement and feedback device 400 can include an RFID tag reader to detect the unique RFID tag (strut ID) for a particular strut. In a third embodiment, each strut of the external fixator 202 can include a Quick Response (QR) code, barcode, or other similar scannable marking that can identify a unique strut ID for each strut. The strut measurement and feedback device 400 can include a bar code or other code scanner to read the scannable code provided on each strut to determine the strut ID for each strut. In various embodiments, each strut of the external fixator 202 can be identified by a separate or unique strut number, or strut ID. In various embodiments, the features of each strut of the external fixator 202 used to identify strut ID's for each strut may be coupled to the external fixator 202 in various locations and is not necessarily limited to being affixed or adhered to the strut.

Figure 5:
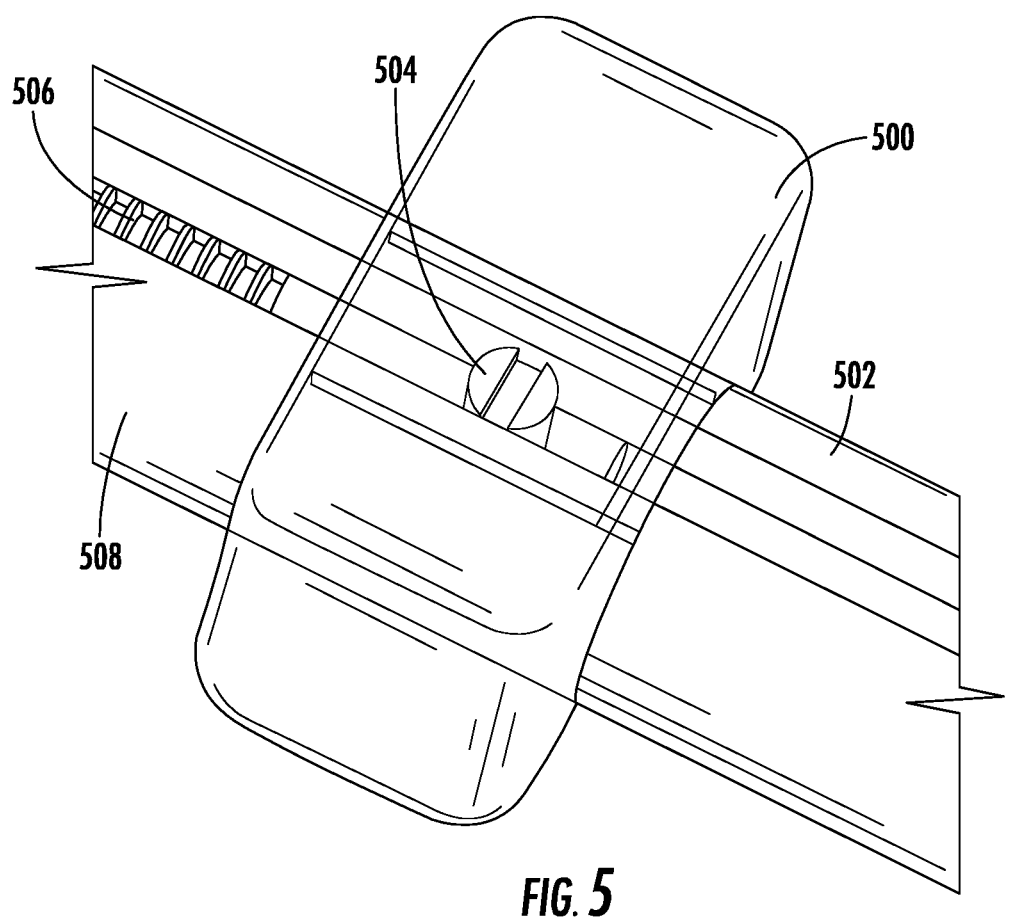
FIG. 5 illustrates a second embodiment of the strut measurement and feedback device depicted in FIGS. 2 and 3.

FIG. 5 illustrates a second embodiment of a strut measurement and feedback device 500. The strut measurement and feedback device 500 may represent the strut measurement and feedback device 204 as depicted in FIGS. 2 and 3. As shown in FIG. 5, the strut measurement and feedback device 500 is coupled to a strut 502. The strut 502 can be a strut of the external fixator 202 as depicted in FIG. 2.

The strut measurement and feedback device 500 may represent an alternative arrangement, form factor, or design of the strut measurement and feedback device 400. In various embodiments, the strut measurement and feedback device 500 may include the same or similar components and may provide the same or similar functionalities as the strut measurement and feedback devices 204 and 400. As shown in FIG. 5, the strut measurement and feedback device 500 is positioned over a strut pin 504 that can be used to detect an absolute position of the strut 502 as described above in relation to the strut measurement and feedback device 400. The strut pin 504 can be coupled to an inner rod component 506 of the strut 502. The strut 502 can further include an outer body component 508.

Figure 6:
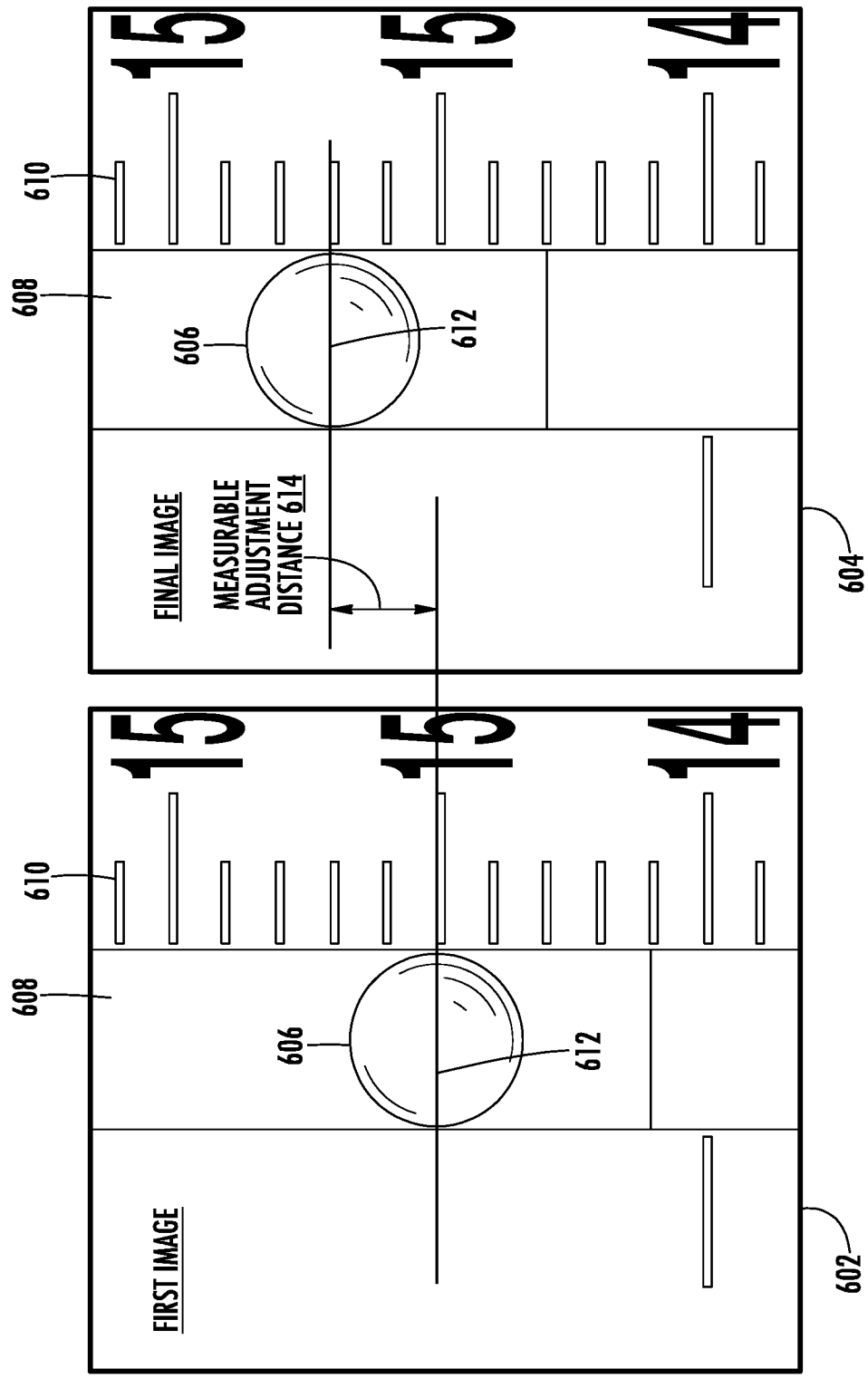
FIG. 6 illustrates various example images captured by the strut measurement and feedback device depicted in FIGS. 2 and 3.

FIG. 6 illustrates an example first image 602 and an example second image 604 that can be captured by a camera of a strut measurement and feedback device (e.g., the strut measurement and feedback device 204, 400, or 500) to detect movement of a strut pin 606. The strut pin 606 can be part of or can be coupled to a strut 608 (e.g., an inner rod component of a strut). The strut 608 can represent a strut of the external fixator 202. Adjacent to the strut pin 606 can be a scale 610 (e.g., a laser etched graduated scale as described herein). The scale 610 can be positioned on a portion of the outer body component of the strut 608.

The first image 602 can represent a position of the strut pin 606 and the strut 608 in a first or initial position. The second image 604 can represent a position of the strut pin 606 and the strut 608 in a second or subsequent position after being moved (e.g., after a length of the strut 608 has been adjusted or changed). For each image 602 and 604, the strut measurement and feedback device 204 can detect an absolute position of the strut 608 based on determining a position of the strut pin 606—for example, by comparing a midpoint 612 of the strut pin 606 to the scale 610. The midpoint 612 of the strut pin 606 can be determined by image processing or analysis capability of the strut measurement and feedback device 204 and/or the user device 206.

The strut measurement and feedback device 204 can also detect an amount of movement (e.g., a linear distance measurement) of the strut pin 606 (and therefore the strut 608) by determining an adjustment distance 614 between a position of the strut pin 606 in the first image 602 and the strut pin 606 in the second image 604. In this manner, the strut measurement and feedback device 204 can determine an absolute and/or relative position of each strut of the external fixator 202 in real-time as adjustments to the strut 608 are made and captured visually.

Figure 7:
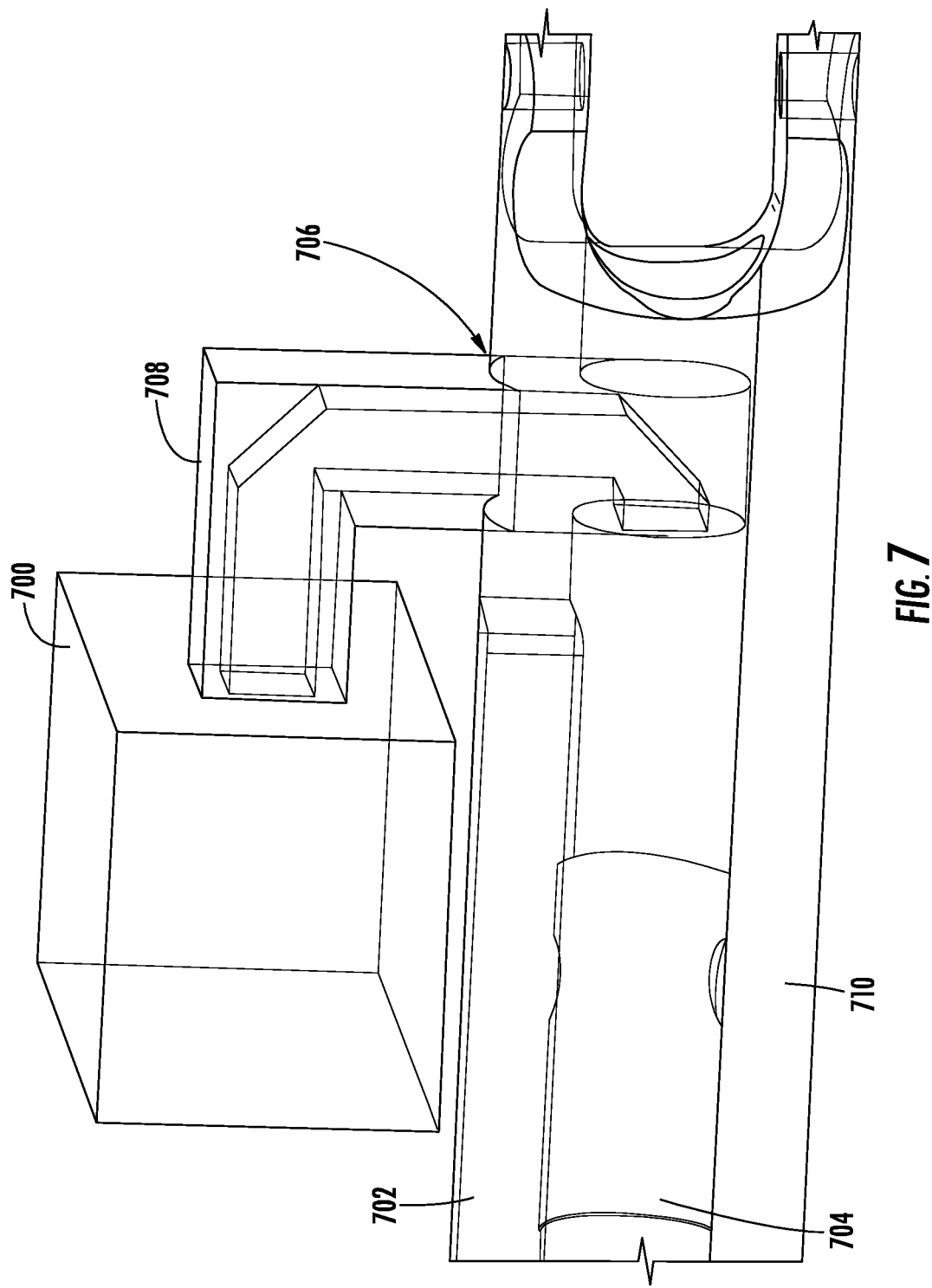
FIG. 7 illustrates a third embodiment of the strut measurement and feedback device depicted in FIGS. 2 and 3.

FIG. 7 illustrates a third embodiment of a strut measurement and feedback device 700. The strut measurement and feedback device 700 may represent the strut measurement and feedback device 204 as depicted in FIGS. 2 and 3. As shown in FIG. 7, the strut measurement and feedback device 700 is coupled to a strut 702. The strut 702 can be a strut of the external fixator 202 as depicted in FIG. 2. The strut 702 can include an outer body component 710. Positioned within an interior of the strut 702 can be a rod 704 (e.g., a threaded rod) that can be moved relative to the outer body component 710.

The strut measurement and feedback device 700 can include an ultrasonic measuring device or component to determine a length of the strut 702 (and/or a position of the rod 704). As shown in FIG. 7, the strut 702 can include an opening or window 706 that can accept an arm or extension component 708 of the strut measurement and feedback device 700. The arm component 708 can be positioned within the opening 706 and can be oriented or aligned with the open inner interior of the strut 702. The strut measurement and feedback device 700 can generate and transmit an ultrasonic signal along the inner portion of the strut 702. The ultrasonic signal can be routed into the interior of the strut 702 by the arm component 708.

The ultrasonic signal transmitted by the strut measurement and feedback device 700 can reach an end of the rod 704 and can then be reflected back toward the arm component 708. The arm component 708 can route the reflected signal to an ultrasonic sensor of the strut measurement and feedback device 700. The strut measurement and feedback device 700 can then determine a linear distance measurement related to the strut 702 and/or the rod 704 based on the amount of time between transmitting the ultrasonic signal and receiving the reflected signal. In various embodiments, the position of the rod 704 within the strut 702 can be determined so as to determine an absolute length of the strut 702 and/or the rod 704. The determined measurement and/or position data can then be provided to the user device 206.

In various embodiments, the end of the rod 704 can be flat (e.g., as shown in FIG. 7). In other embodiments, the end of the rod 704 can be have a different shape or geometry such as, for example, spherical to enhance the reflected ultrasonic signal. In various embodiments, the ultrasonic signal can be transmitted, and the reflected signal received, at an end of the arm component 708 positioned with the opening 706. Under such scenarios, the ultrasonic sensor may be oriented in line with the inner diameter of the strut 702. In other embodiments, the ultrasonic signal can be transmitted, and the reflected signal received, using ultrasonic deflectors that may be provided within the arm component 708 (e.g., as shown in FIG. 7). Under such scenarios, the deflectors allow for "bouncing" of the reflected signal at different angles until the reflected signal travels up into the arm component 708 and back toward the main body of the strut measurement and feedback device 700.

In various embodiments, as an alternative to transmitting ultrasonic signals for measuring distance and/or position, the strut measurement and feedback device 700 can include a laser measurement device or component. The laser measurement component can operate in a similar manner as described above in relation to the ultrasonic measurement component while transmitting and detecting a laser signal reflected off of the rod 704.

Figure 8:
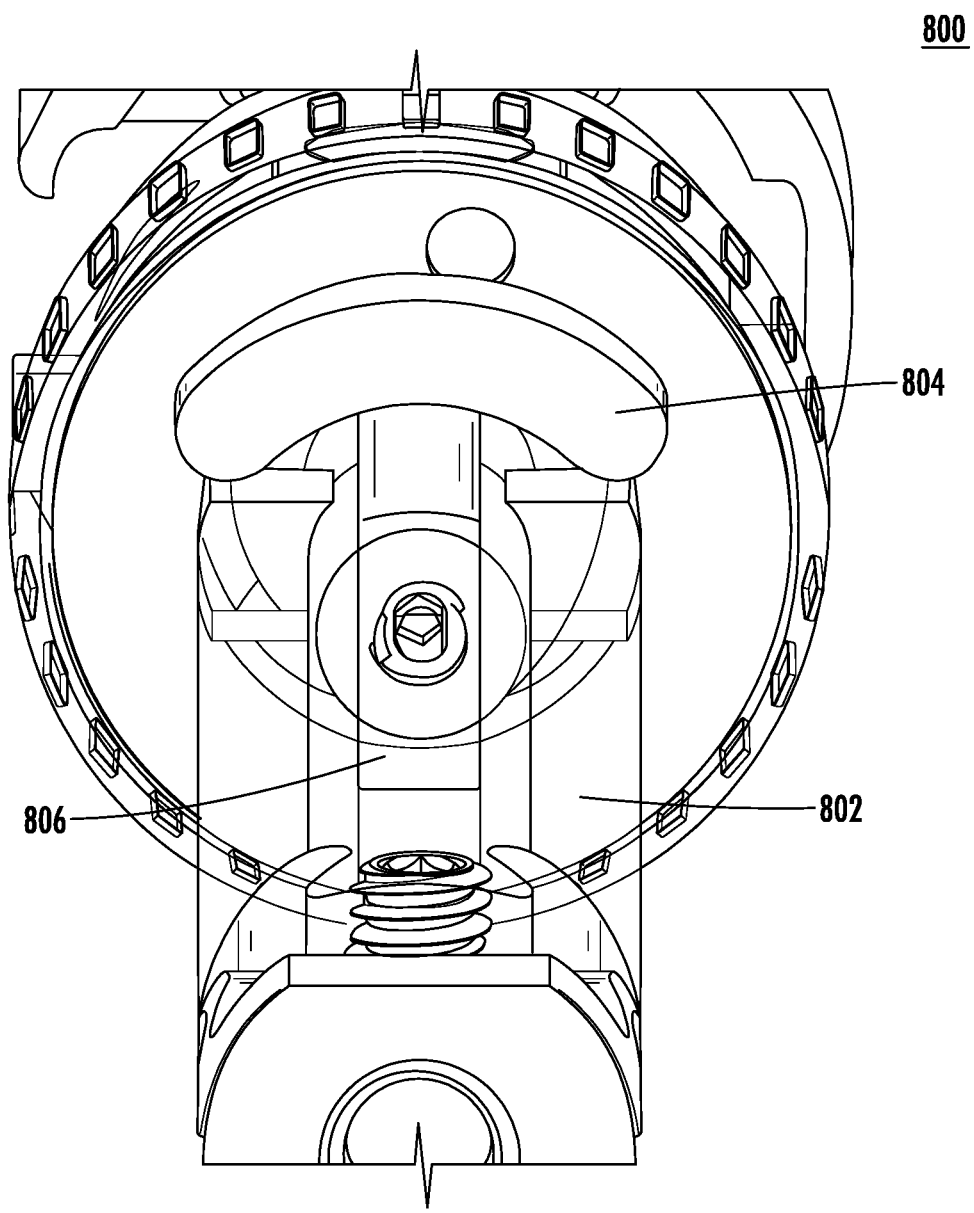
FIG. 8 illustrates a first view of an embodiment of a strut of an external fixator depicted in FIG. 2 in accordance with one aspect of the present disclosure.

FIG. 8 illustrates a first view of an example embodiment of a strut 802. The strut 802 can be a strut of the external fixator 202 as depicted in FIG. 2. In contrast to current struts, the strut 802 can include a strut pin 804 that extends beyond an outer perimeter of the strut 802—for example, extending out of a slot 806 of the strut 802. As shown in FIG. 8, the strut pin 804 extends out of the slot 806 and wraps around or covers a portion of the outer diameter of the strut 802. By doing so, the strut pin 804 allows for a strut measurement and feedback device (e.g., the strut measurement and feedback device 204) to measure movement of the strut pin 802 from a fixed attachment point on the strut 802.

Specifically, the strut measurement and feedback device 204 can be attached to a fixed position on the strut 802 and aimed at the strut pin 804, which acts as a position target. The strut measurement and feedback device 204 can be placed on either side of the strut pin 804 and can implement any distance measuring technique such as, for example, ultrasonic, laser, or a similar technique to measure the distance to the strut pin 804 and/or movement of the strut pin 804.

Figure 9:
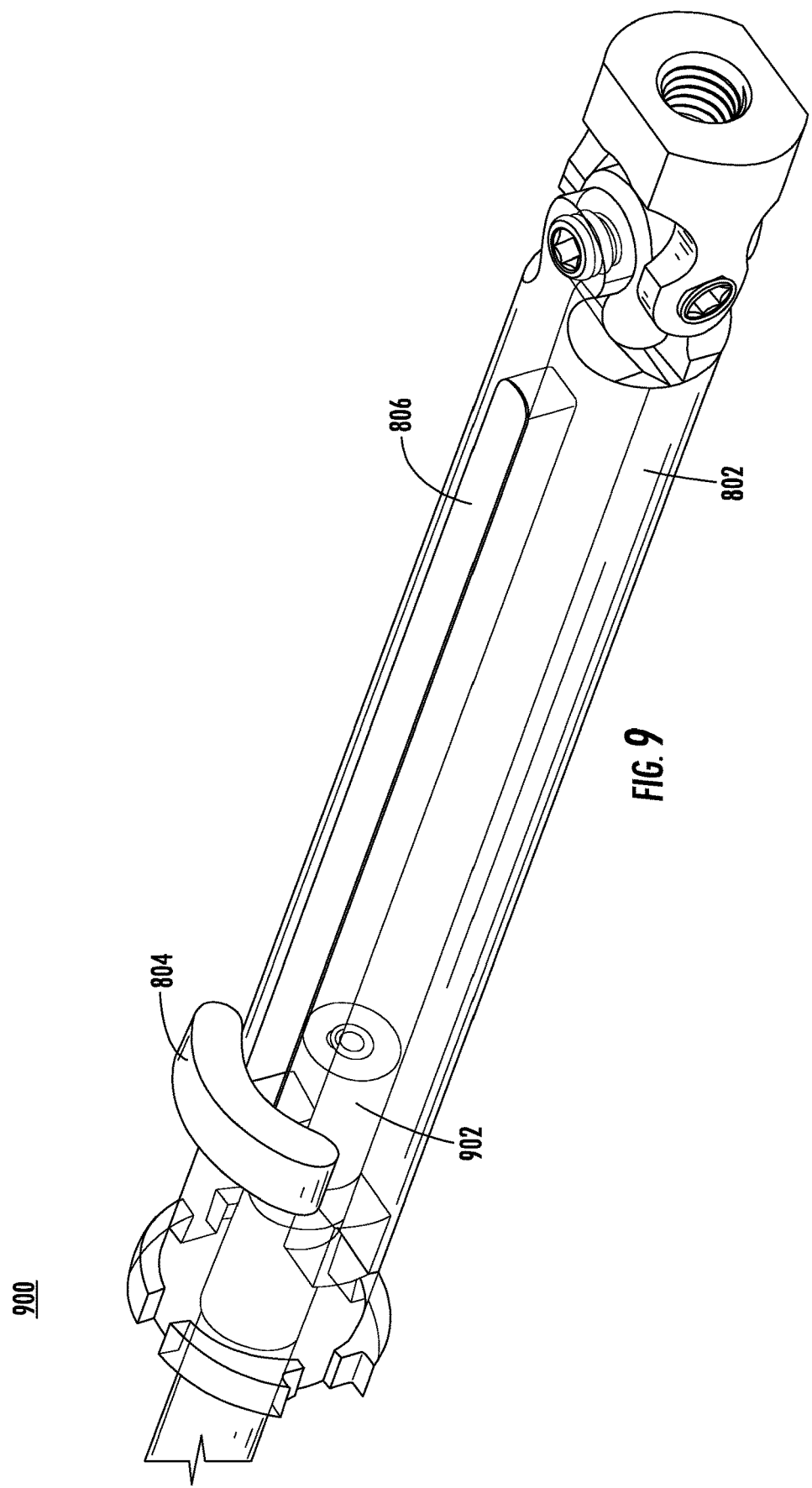
FIG. 9 illustrates a second view of the strut depicted in FIG. 8.

FIG. 9 illustrates a second view of the strut pin 804 extending from the slot 806 of the strut 802. The strut pin 804 can be relatively large to provide a large target for the distance measurement component of the strut measurement and feedback device 204, thereby ensuring accurate distance measurements without the need to move the strut measurement and feedback device 204 along the length of the strut 802. As shown in FIG. 9, the strut pin 804 is coupled to an inner rod component 902 positioned within an interior of the strut 802.

Figure 10:
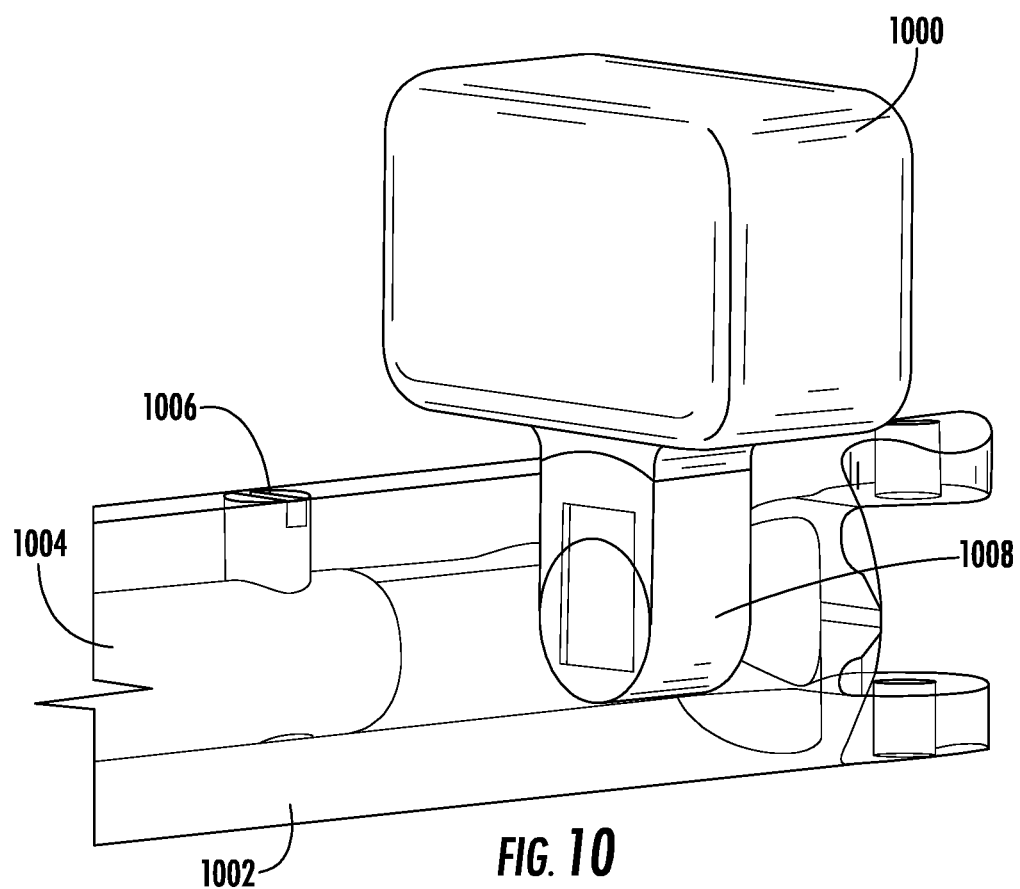
FIG. 10 illustrates a fourth embodiment of the strut measurement and feedback device depicted in FIGS. 2 and 3.

FIG. 10 illustrates a fourth embodiment of a strut measurement and feedback device 1000. The strut measurement and feedback device 1000 may represent the strut measurement and feedback device 204 as depicted in FIGS. 2 and 3. As shown in FIG. 10, the strut measurement and feedback device 1000 is coupled to a strut 1002. The strut 1002 can be a strut of the external fixator 202 as depicted in FIG. 2. Positioned within an interior of the strut 1002 can be a rod 1004 (e.g., a threaded rod). A strut pin 1006 can be coupled to the rod 1004. The rod 1004 can be moved relative to an outer body component of the strut 1002.

The strut measurement and feedback device 1000 can include an infrared measuring device or component to determine a length of the strut 1002 (and/or a position of the rod 1004). Similar to the strut measurement and feedback device 700, the strut measurement and feedback device 1000 can include a portion or component 1008 positioned within an inner diameter of the strut 1002. The infrared measuring component of the strut measurement and feedback device 1000 can generate and transmit an infrared signal that can be reflected off an end of the rod 1004 to determine a length of the strut 1002 and/or a position of the rod 1004. As an alternative to using the bottom of the rod 1004 as the target for the infrared signal, the strut measurement and feedback device 1000 can be used in conjunction with the enhanced strut pin 804 as shown in FIGS. 8 and 9 as will be appreciated by one of ordinary skill in the relevant art. In general, the strut measurement and feedback device 1000 can be attached to a fixed location on the strut 1002 and can measure a distance to a target—for example, the rod 1004—to determine an absolute length of the strut 1002.

In an embodiment, the strut measurement and feedback device 204 can include a camera that can visualize the threads of a strut of the external fixator 202 as the threads turn. Under such a scenario, a window or opening can be provided in the body of each strut of the external fixator 202 to provide a view of the threads of the rods. Based on viewing the movement of the threads, the strut measurement and feedback device 204 can provide feedback on how far a specific thread has rotated, which can be used to determine a linear distance travelled by the strut given the known pitch of the threaded rod. As a further embodiment, threaded rods of the external fixator 202 can include distinguishing features or markings to enable an absolute movement of each strut of the external fixator 202 to be determined. The distinguishing features or markings can include features provided directly on the threads. Alternatively, a surface one each rod can be cut down the length of the threaded rod and the surface could be laser marked with numerical lengths or other unique markings.

In a further embodiment, when the strut measurement and feedback device 204 includes a camera that can visualize the threads of a strut of the external fixator 202, the strut measurement and feedback device 204 can further include or be paired with a position sensor (e.g., a position sensor as described in relation to any of the embodiments described herein). The position sensor can confirm that the strut length is within a general range and the camera can provide additional feedback to the user to define a higher resolution of the position of a strut.

In another embodiment, the strut measurement and feedback device 204 can include one or more Hall effect sensors that can be used to determine the length of each strut of the external fixator 202. As an example, a permanent magnet can be attached to a fixed location on a threaded rod within the strut body and one or more Hall effect sensors can be held in stationary positions outside of the strut body. The magnet can move closer or further from the corresponding one or more Hall effect sensors as the rod is moved. The movement of the magnet can be detected by the one or more Hall effect sensors which can determine a linear distance of movement of the strut based on the detected magnetic field changes. In an embodiment, multiple Hall effect sensors can be positioned along the outside of the strut body.

Figure 11:
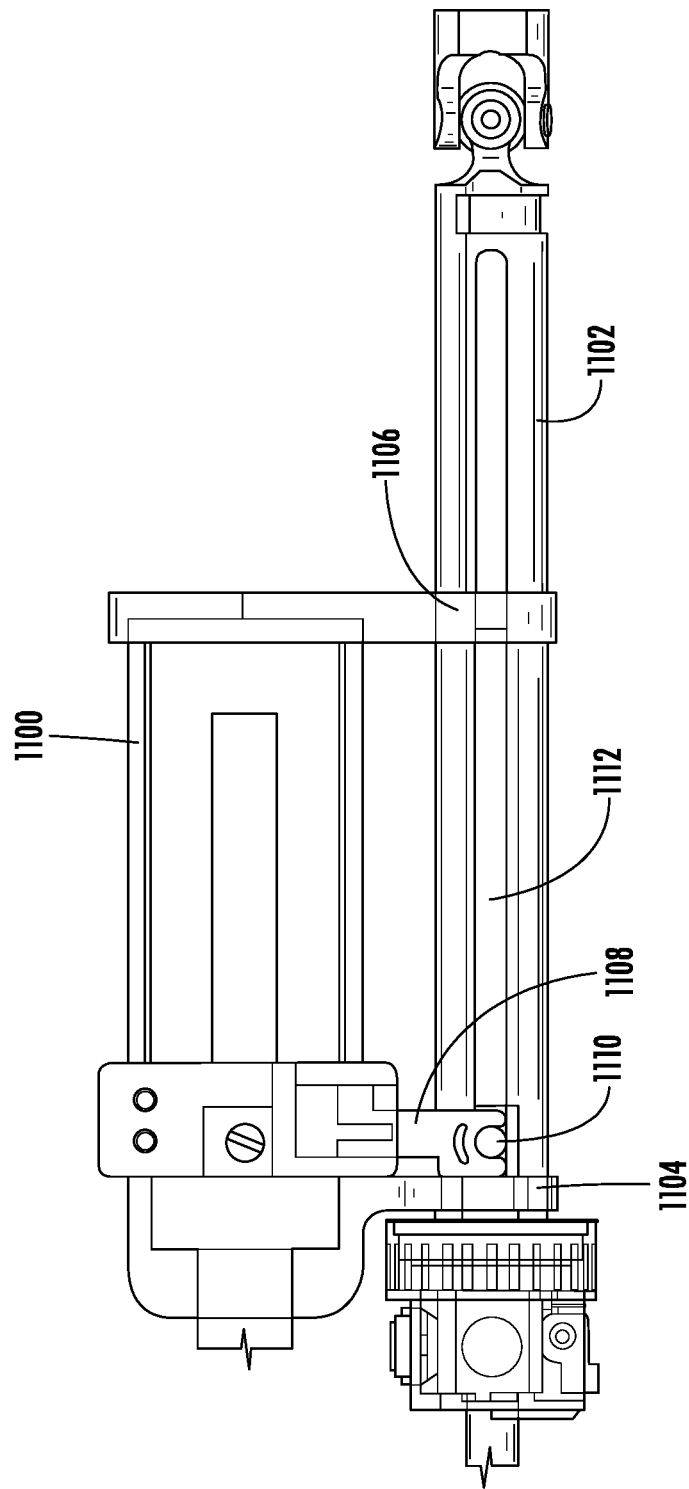
FIG. 11 illustrates a fifth embodiment of the strut measurement and feedback device depicted in FIGS. 2 and 3.

FIG. 11 illustrates a fifth embodiment of a strut measurement and feedback device 1100. The strut measurement and feedback device 1100 may represent the strut measurement and feedback device 204 as depicted in FIGS. 2 and 3. As shown in FIG. 11, the strut measurement and feedback device 1100 is coupled to a strut 1102. The strut 1102 can be a strut of the external fixator 202 as depicted in FIG. 2.

The strut measurement and feedback device 1100 may be or may include a membrane potentiometer that can measure the displacement of a pin 1110 within a slot 1112 of the strut 1102. As shown in FIG. 11, the strut measurement and feedback device 1100 can be attached to the outside of the body of the strut 1102 at a first position 1104 and a second position 1106. The strut measurement and feedback device 1100 can be oriented at an angle with respect to the body of the strut 1102. In an embodiment, the strut measurement and feedback device 1100 can be oriented parallel to an axis of the strut 1102.

The membrane potentiometer of the strut measurement and feedback device 1100 can provide a linear measurement based on a voltage output that corresponds to where pressure is applied along the length of the membrane potentiometer. A mechanical or magnetic linkage 1108 between the pin 1110 of the strut 1102 and a pin that applies pressure to the membrane potentiometer would ensure that when the strut pin 1110 moves, the membrane potentiometer pin also moves along the length of the membrane potentiometer, giving a linear distance measurement. In an embodiment, the strut measurement and feedback device 1100 can include multiple attachment points to obviate the need for the strut measurement and feedback device 1100 to cover the entire length of the strut 1102. As an example, with two or more attachment points, the strut measurement and feedback device 1100 can be reduced in length and can be attached to whichever attachment point is closest to the moving pin 1110 in the slot 1112 of the strut 1102.

Figure 12:
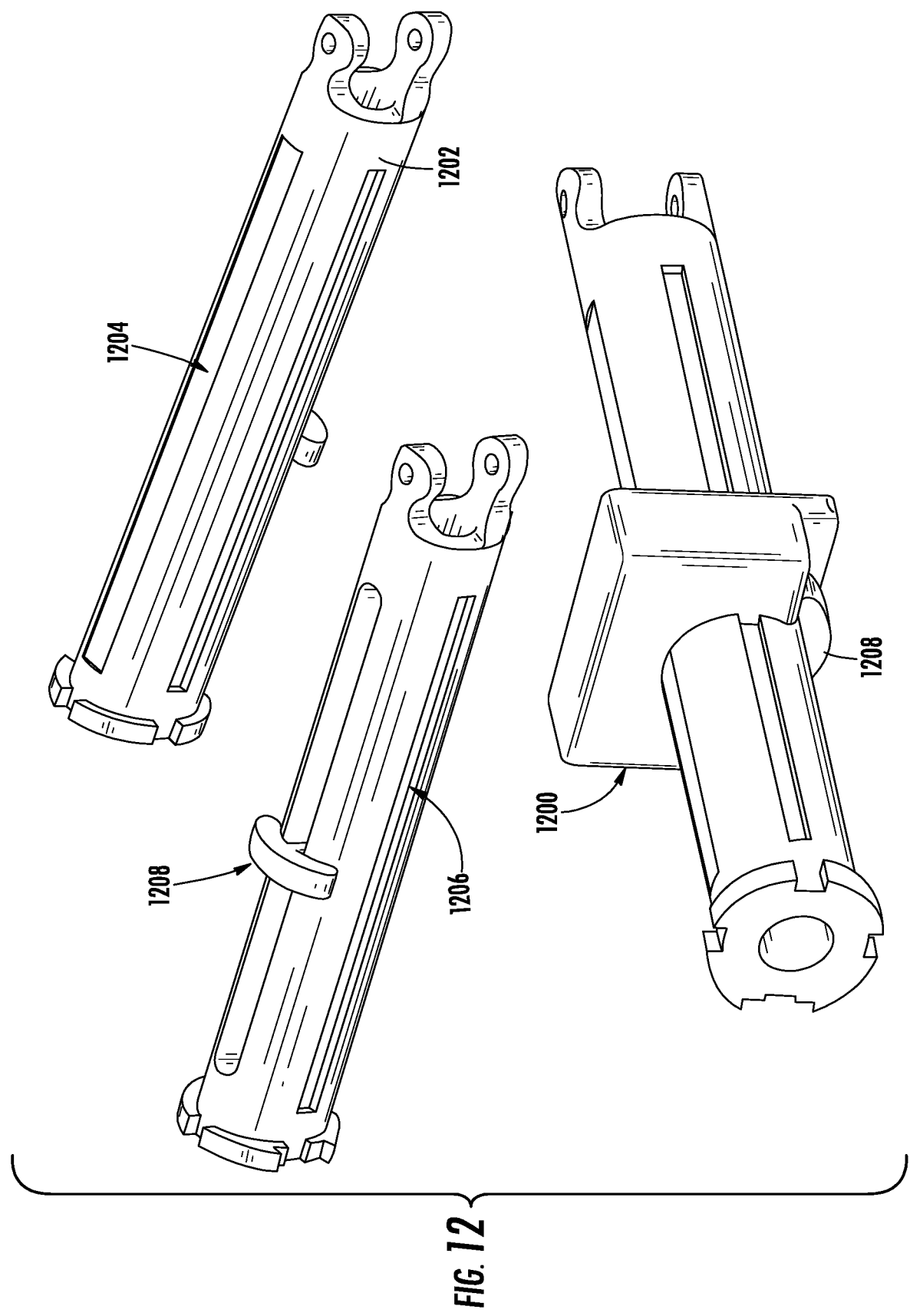
FIG. 12 illustrates a sixth embodiment of the strut measurement and feedback device depicted in FIGS. 2 and 3.

FIG. 12 illustrates a sixth embodiment of a strut measurement and feedback device 1200. The strut measurement and feedback device 1200 may represent the strut measurement and feedback device 204 as depicted in FIGS. 2 and 3. As shown in FIG. 12, the strut measurement and feedback device 1200 is coupled to a strut 1202. The strut 1202 can be a strut of the external fixator 202 as depicted in FIG. 2.

The strut measurement and feedback device 1200 may be or may include a linear encoder that can be used to measure a length of the strut 1202. The linear encoder can be any type of liner encoder including, for example, a magnetic, an optical, an inductive, or a capacitive linear encoder. The linear encoder can include a sensing head that moves along a scale bar. For example, an optical linear encoder can use a light source and a photo-detector to determine the position of the sensing head on the scale bar. A magnetic linear encoder can use a magnetic coupling between the sensing head and a magnetic scale bar. A capacitive or inductive linear encoder can use metal plates embedded in the scale bar that are arranged in a specific pattern that are read by the sensing head.

In general, capacitive and inductive linear encoders can be made with scales that are incremental or absolute. The incremental scales typically have a smaller footprint than the absolute scale. The strut measurement and feedback device 1200 can be used with either an incremental scale or an absolute scale. An absolute measurement of a length of the strut 1202 can be made with an incremental scale if a user of the strut measurement and feedback device 1200 initially slides the strut measurement and feedback device 1200 to a hard stop at one end of the strut 1202 to "zero" the linear encoder prior to taking measurements. Alternatively, the user could slide the strut measurement and feedback device 1200 onto the scale bar in a specific manner every time the strut measurement and feedback device 1200 is used, such that the linear encoder begins reading the scale bar in the same spot each time it is used.

In an embodiment, to reduce the length of the scale bar that may be required, two attachment points could be used on the strut 1202. For example, a first attachment point above a slot of the strut 1202 can be used with a second attachment point below the slot of the strut 1202. The user of the strut measurement and feedback device 1200 can then attach the strut measurement and feedback device 1200 to whichever end of the strut 1202 is closer to a pin positioned in a slot of the strut. In another embodiment, the scale bar could be configured to slide or fold. Accordingly, when the user is measuring shorter struts, the user would not have to fold or slide out the scale bar fully and would only extend the scale fully if the user were measuring relatively longer struts.

FIG. 12 illustrates several views of the strut 1202 and a version of the strut measurement and feedback device 1200 that uses an embedded scale 1204 that is included into the strut 1202. The strut can include a slot 1206 that can be used to attach the strut measurement and feedback device 1200 to the strut 1202. The strut measurement and feedback device 1200 can then slide over the embedded scale 1204. The strut 1202 can further include a modified tracking pin 1208. The strut measurement and feedback device 1200 can be coupled or attached either mechanically or magnetically to the modified tracking pin 1208. The version of the strut measurement and feedback device 1200 shown in FIG. 12 can avoid issues related to the length of the scale and the different lengths of each strut being measured by using, for example, the embedded scale 1204.

In an embodiment, the strut measurement and feedback device 204 can be coupled to a first feature on a stationary portion of the strut 202 (e.g., the outer body of the strut 202) and to a second feature on a translating portion of the strut 202 (e.g., the inner threaded rod of the strut 202). Using attachments to the stationary and translating components of the strut 202 allows strut measurement and feedback device 204 to be used with struts having any length. Any of the described embodiments of the strut measurement and feedback device 204 described herein can be modified to use this attachment configuration.

Figure 13:
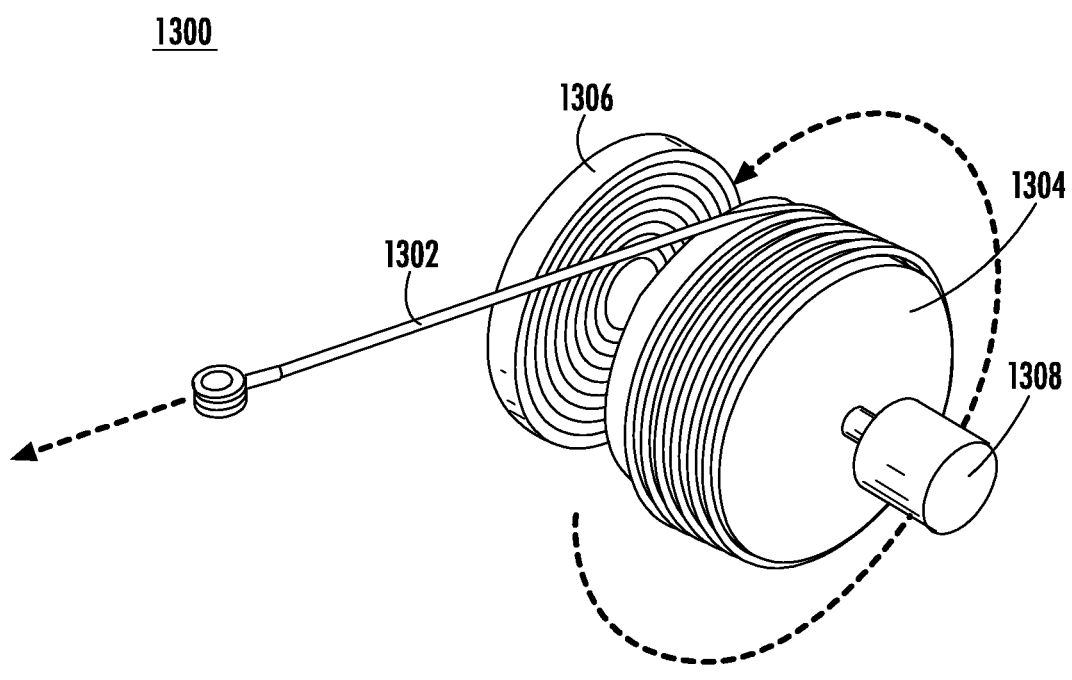
FIG. 13 illustrates a seventh embodiment of the strut measurement and feedback device depicted in FIGS. 2 and 3.

FIG. 13 illustrates a seventh embodiment of a strut measurement and feedback device 1300. The strut measurement and feedback device 1300 may represent the strut measurement and feedback device 204 as depicted in FIGS. 2 and 3. The strut measurement and feedback device 1300 may be or may include a string potentiometer that can be used to a measure a length of a strut (e.g., a strut of the external fixator 202).

As shown in FIG. 13, strut measurement and feedback device 1300 can include a cable 1302 (e.g., a string, a wire, or a flexible high strength cable) wrapped around a spool 1304. The spool 1304 can be a constant diameter spool. The spool 1304 can be spring loaded based on a spring 1306. The spring 1306 can be a high torque, long life power spring. The spool 1302 can be coupled to a rotational sensor 1308.

During operation—for example, when the cable 1302 extends or retracts—the rotational sensor 1308 can determine a linear travel distance of the cable 1302 based on rotation of the spool 1304. In various embodiments, the strut measurement and feedback device 1300 can be coupled to a strut (e.g., a strut of the external fixator 202) such that the spool 1304 is attached to an outside of the strut and the cable 1302 is routed through an opening or window in the strut and coupled to a threaded rod of the strut. Accordingly, as the threaded rod is moved, the sensor 1308 can determine a length of the strut based on the movement of the cable 1302 and rotation of the spool 1304.

In an alternative embodiment, the spool 1304 can be fixed to the outside of the strut and the cable 1302 can be attached to a strut pin positioned within a slot of the strut. Overall, the strut measurement and feedback device 1300 provides for a wide range of mounting and use configurations since the cable 1302 can be routed around objects and can make 180 degree turns.

Figure 15:
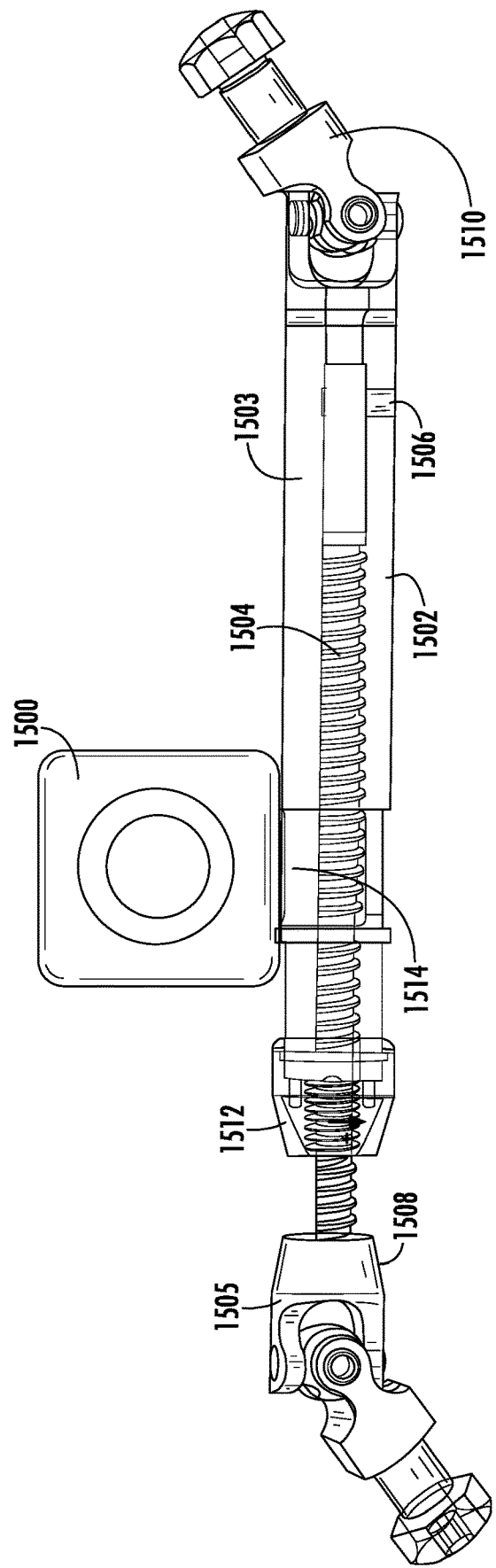
FIG. 15 illustrates an eighth embodiment of the strut measurement and feedback device depicted in FIGS. 2 and 3.

FIG. 15 illustrates an eighth embodiment of a strut measurement and feedback device 1500. The strut measurement and feedback device 1500 may represent the strut measurement and feedback device 204 as depicted in FIGS. 2 and 3. As shown in FIG. 15, the strut measurement and feedback device 1500 is coupled to a strut 1502. The strut 1502 can be a strut of the external fixator 202 as depicted in FIG. 2. The strut 1502 may include a first outer body or member 1503, a second outer body or member 1505, and an externally threaded rod 1504 coupled to the first and second outer bodies 1503, 1505, although the strut may be any suitable strut now known or hereafter developed. A strut pin 1506 can be used to couple the first outer body 1503 to the rod 1504. Thus arranged, as will be appreciated by one of ordinary skill in the art, rotation of the rod 1504 causes the second outer body 1505 to move relative to the first outer body 1503.

As further shown in FIG. 15, the second outer body 1505 may be in the form of a first joint 1508 such as, but not limited to, a universal joint or the like and the first outer body 1503 may be attached to a second joint 1510 such as, but not limited to a universal joint or the like. The first joint 1508 may be attached to a first ring or base of a bone alignment device (e.g., the first ring 102 of the bone alignment device 100 depicted in FIG. 1). The second joint 1508 may be attached to a second ring or base of a bone alignment device (e.g., the second ring 104 of the bone alignment device 100 depicted in FIG. 1). The strut 1502 may also include an actuator 1512 operatively coupled to the first outer body 1503 and/or the rod 1504. In use, rotation of the actuator 1512 causes the rod 1504 to rotate to move the first ring or base of a bone alignment device relative to the second ring or base of the bone alignment device, thereby extending or reducing a distance between to the first and second rings of a bone alignment device based on a direction of rotation of the actuator 1512.

Figure 16:
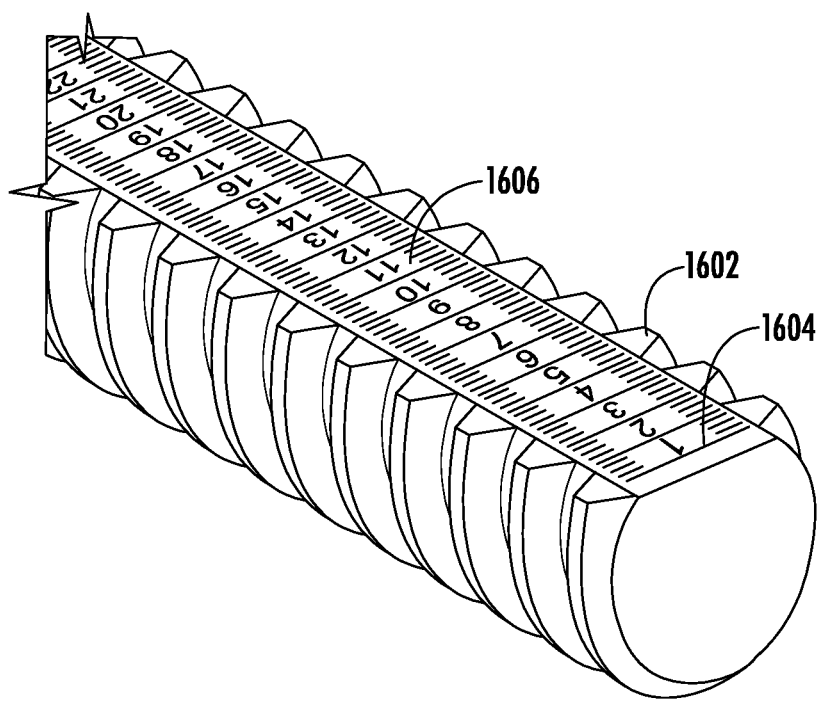
FIG. 16 illustrates an embodiment of a threaded rod used in connection with the embodiment of the strut measurement and feedback depicted in FIG. 15.

FIG. 16 illustrates a detailed, perspective view of an example of an embodiment of a portion of the rod 1504. As shown, the rod 1504 may include threads 1602 for threadably engaging the first body member 1503 and a non-circular or cut surface 1604. The non-circular surface 1604 may be a substantially flat surface. The non-circular surface 1604 may extend the entire length of the rod 1504. Alternatively, the non-circular surface 1604 may extend only a portion thereof. Thus arranged, the rod 1504 may have a non-circular cross-sectional shape such as, for example, a D-shaped cross-section. As shown, the threads 1602 may be positioned on an outer portion of the rod 1504 that has a circular shape.

Referring to FIGS. 15 and 16, an inner diameter of the first outer body 1503 of the strut 1502 may include a corresponding non-circular cross-sectional shape as the rod 1504, such that the non-circular cross-sectional shape of the rod 1504 may serve as an anti-rotational feature to prevent the rod 1504 from rotating relative to the first outer body 1503 of the strut 1502. In an embodiment, the non-circular cross-sectional shape of the rod 1504 may be the only anti-rotation feature preventing rotation of the rod 1504. In another embodiment, the pin 1506 may be positioned to ride along a slot formed in the first outer body 1503 of the strut 1502 to provide a further anti-rotation mechanism, as described herein. Under either scenario, the rod 1504 and the first outer body 1503 of the strut 1502 may be prevented from rotating relative to each other. As a result, rotation of the actuator 1512 about the first outer body 1503 of the strut 1502 is translated into a translational movement of the rod 1504 relative to the first outer body 1503 along a long axis or length of the rod 1504 and the strut 1502.

As shown in FIG. 16, the non-circular surface 1604 of the rod 1504 may include markings 1606. The markings 1606 may be used to determine and/or indicate a length of the rod 1504. In an embodiment, the markings 1606 may form a measurement scale or may form another pattern for denoting a length of the strut 1502 (e.g., distance between the second body member 1505 and the first outer body 1503). Referring to FIG. 15, the strut measurement and feedback device 1500 may be operatively coupled to the strut 1502 and positioned over a slot 1514 formed in the first outer body 1503. The slot 1514 may be a hole or opening that enables visualization of the markings 1606 formed on the non-circular surface 1604 of the rod 1504. In an embodiment, the strut measurement and feedback device 1500 may include a camera or other device to visualize, detect, read, identify, etc. (used interchangeably herein without the intent to limit) the markings 1606 formed on the non-circular surface 1604 of the rod 1504. Accordingly, as the rod 1504 is moved relative to the first outer body 1503 of the strut 1502, the strut measurement and feedback device 1500 may visualize the markings 1606 and may directly measure the adjusted length of the rod 1504.

Figure 17:
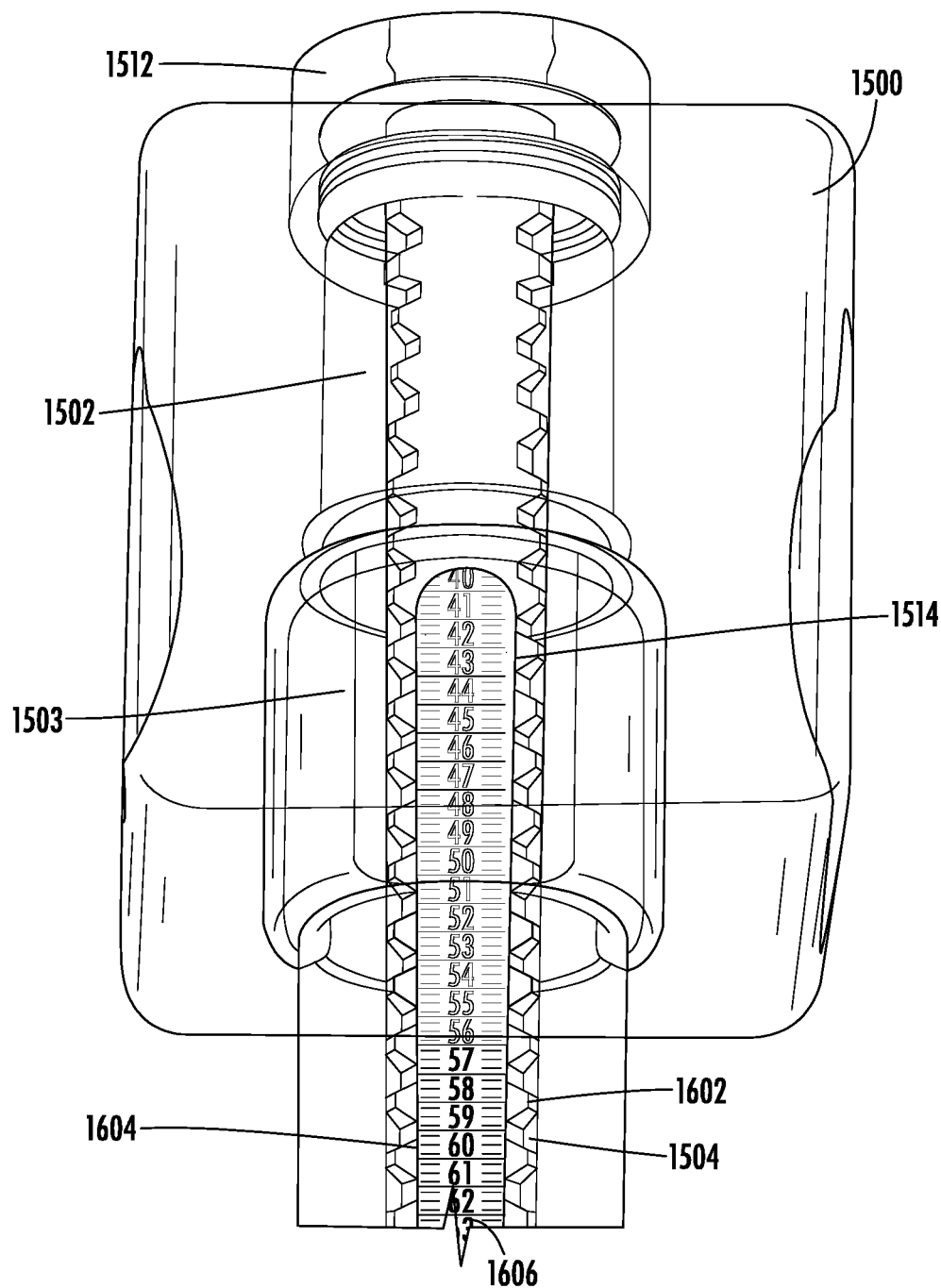
FIG. 17 illustrates a perspective, top view of the embodiment of the strut measurement and feedback device depicted in FIG. 15.

FIG. 17 illustrates a top view of the strut measurement and feedback device 1500 positioned over the slot 1514 with the strut measurement and feedback device 1500 shown in transparent form for better clarity. As shown, the strut measurement and feedback device 1500 can visualize the markings 1606 formed on the non-circular surface 1604 of the rod 1504.

Referring to FIGS. 16 and 17, the markings 1606 positioned on the non-circular surface 1604 allow the strut measurement and feedback device 1500 to be connected to the strut 1502 at a fixed location—for example, over the slot 1514 such that the strut measurement and feedback device 1500 may always visualize the markings 1606 as the length of the rod 1504 is adjusted. This enables a user of the strut measurement and feedback device 1500 to always attach the strut measurement and feedback device 1500 to the same location on each strut of a bone alignment device, with such repetition improving usability of the strut measurement and feedback device 1500 and improving accurate determinations of the length of the rod 1504.

In an embodiment, the first outer body 1503 of the strut 1502 may include a second slot (not shown) that may aid anti-rotation as described herein—for example, to accommodate use of the pin 1506. In general, the first body 1503 of the strut 1502 may include any number of slots. The slots can have any width and any length, may have the same or different widths and lengths, and may be positioned along any portion of the body 1503 of the strut 1502. In an embodiment, at least one slot is wide enough for an individual to visualize the markings 1606 without the use of the strut measurement and feedback device 1500.

FIGS. 18A-18D illustrates a ninth embodiment of a strut measurement and feedback device 1800. The strut measurement and feedback device 1800 may represent the strut measurement and feedback device 204 as depicted in FIGS. 2 and 3. As shown in FIGS. 18A-18D, the strut measurement and feedback device 1800 is coupled to a strut 1802. The strut 1802 can be a strut of the external fixator 202 as depicted in FIG. 2. The strut 1802 may include a first outer body or member 1804, a second outer body or member 1808, and an externally threaded rod 1806 coupled to the first and second outer bodies 1804, 1806, although the strut may be any suitable strut now known or hereafter developed. Thus arranged, as will be appreciated by one of ordinary skill in the art, rotation of the actuator causes the second outer body 1808 to move relative to the first outer body 1804.

The strut measurement and feedback device 1800 may include any of the features, capabilities, and/or components of any other strut measurement and feedback device described herein. For example, in an embodiment, the strut measurement and feedback device 1800 may include the ability to identify a strut (e.g., distinguish the strut 1802 from any other strut of a bone alignment device) and may include the ability to determine an absolute length of the strut 1802 (e.g., relative distance between the second outer body 1808 and the first outer body 1804) using any of the features, capabilities, or components described in relation to any other strut measurement and feedback device described herein. Further, as will be described in greater detail below, the strut measurement and feedback device 1800 may include a device or component for adjusting the length of the strut 1802 such as, for example, a gear 1810 for operatively coupling to the actuator and/or threaded rod of the strut 1802. In an embodiment, the device for adjusting the length of the strut 1802 can be permanently attached and/or integrally formed with the strut measurement and feedback device 1800. In another embodiment, the device for adjusting the length of the strut 1802 can be removably attached to the strut measurement and feedback device 1800.

FIG. 18A illustrates a front view of the strut measurement and feedback device 1800. FIG. 18B illustrates a side view of the strut measurement and feedback device 1800. FIG. 18C illustrates a bottom view of the strut measurement and feedback device 1800. FIG. 18D illustrates a top view of the strut measurement and feedback device 1800.

FIGS. 19A-19D illustrates a tenth embodiment of a strut measurement and feedback device 1900. The strut measurement and feedback device 1900 may represent the strut measurement and feedback device 204 as depicted in FIGS. 2 and 3. As shown in FIGS. 19A-19D, the strut measurement and feedback device 1900 is coupled to the strut 1802.

The strut measurement and feedback device 1900 may include the same or similar components, may provide the same or similar functionalities, and may operate in a similar manner as the strut measurement and feedback device 1800. Accordingly, the strut measurement and feedback devices 1800 and 1900 are described herein together for brevity without any intent to limit. Further, as with the strut measurement and feedback device 1800, the strut measurement and feedback device 1900 may identify a strut to which it is attached, determine the absolute length of the strut, and may include a device or may allow a device to be attached that can adjust a length of the strut.

FIG. 19A illustrates a side view of the strut measurement and feedback device 1900. FIG. 19B illustrates a front view of the strut measurement and feedback device 1900. FIG. 19C illustrates a top view of the strut measurement and feedback device 1900. FIG. 19D illustrates a bottom view of the strut measurement and feedback device 1900.

The strut measurement and feedback devices 1800 and 1900 may be connected to any portion of a strut such as, for example, strut 1802. The strut measurement and feedback devices 1800 and 1900 may include a display or screen 1812, 1902 to display identification information of the strut 1802 and/or to display a measured length of the strut 1802. As described herein, each of the strut measurement and feedback devices 1800 and 1900 may include a device, an instrument, a component, etc. for adjusting the length of the strut 1802 or may include the capability to have such device or component removably attached to each of the strut measurement and feedback devices 1800 and 1900. The device for adjusting the length of the strut may be any suitable tool now known or hereafter developed including, for example, a simple mechanical tool, an automated drive tool, an instrument with any combination of electronics, communication interfaces, and strut adjustment schedules stored in a memory, etc.

In one embodiment, a user can couple the strut measurement and feedback devices 1800 and 1900 to a strut 1802, the strut measurement and feedback devices 1800 and 1900 would identify and measure the absolute length of the connected strut 1802 using any of the mechanism described herein. In addition, the strut measurement and feedback devices 1800 and 1900 would adjust the strut to the appropriate length.

In an embodiment, the strut measurement and feedback devices 1800 and 1900 may contain electronics (e.g., a controller) and memory (such as the memory 314) that may store length adjustments to be made to a strut such as, for example, strut 1802 (e.g., as specified by a prescription). The adjustments to the length of the strut 1802 can then be made automatically based on the stored prescription information. In an embodiment, the strut measurement and feedback devices 1800 and 1900 may determine the amount of adjustment required to the strut 1802 based on a rotary encoder or through real-time measurements of the length of the strut 1802. In various embodiments, the strut measurement and feedback devices 1800 and 1900 may be attached to a portion of the strut 1802 that allows the length of the strut 1802 to be adjusted (e.g., attached to an actuator of the strut 1802). In various embodiments, the strut measurement and feedback devices 1800 and 1900 may communicate with one or more remote devices such as, for example, wirelessly communicating with a smartphone or other electronic device including, for example, a remote user device or another device that can be used to adjust the length of the strut 1802 and/or to identify the strut 1802 or determine the length of the strut 1802. In an embodiment, the strut measurement and feedback devices 1800 and 1900 may be built into the strut 1802 as a permanent component rather than being a detachable device. In an embodiment, the strut measurement and feedback devices 1800 and 900 may include a gear 1810, 1904 that interfaces with the actuator and/or threaded rod of the strut 1802. In use, rotation of the gear 1810, 1904 causes the threaded rod 1806 to move the second outer body 1808 relative to the first outer body 1804 to adjust the overall length of the strut 1802. Rotation of the gear 1810, 1904 may be performed by any suitable mechanism now known or hereafter developed including, for example, hand-rotation, wrench, electronics, etc. In an embodiment, the strut measurement and feedback devices 1800 and 900 may be configured to adjust the length of the strut 1802 by turning the rod 1806 directly.

FIG. 14 illustrates an embodiment of a logic flow 1400 that may be representative of techniques for providing real-time feedback on the compliance of a length of a strut of an external fixator. The logic flow 1400 enables an individual adjusting the length of the strut to efficiently determine if the correct strut is being adjusted and if the adjustment matches that specified by a prescription. The logic flow 1400 may be representative of operations that may be performed by any of the strut measurement and feedback devices with or without corresponding user devices, as described and/or depicted herein. Without the intent to limit, the logic flow 1400 is described herein with reference to the components of the compliance monitoring system 200 as depicted in FIG. 2.

At block 1402, the strut measurement and feedback device 204 can be attached to a strut of the external fixator 202. Prior to being attached or after being attached to the strut of the external fixator, the strut measurement and feedback device 204 can determine the strut to which it is attached. Accordingly, the strut measurement and feedback device 204 can determine an identification (strut ID) of the strut to which it is coupled. In use, the strut measurement and feedback device 204 can determine which strut it is coupled to by any now known or hereafter developed mechanisms including, for example, those described herein. Further, the strut measurement and feedback device 204 can provide an indication or signal when the strut measurement and feedback device 204 is properly positioned on the strut.

At block 1404, the strut measurement and feedback device 204 can detect an adjustment made to the length of the strut to which it is attached. The strut measurement and feedback device 204 can determine an absolute and/or a relative measurement of the length of the strut. The strut measurement and feedback device 204 can determine an initial length of the strut prior to adjustment, an ending length of the strut after the adjustment, and/or a measure of the change in length of the strut resulting from the adjustment. In use, the strut measurement and feedback device 204 can determine an adjustment made to the length of the strut by any now known or hereafter developed mechanisms including, for example, those described herein.

At block 1406, the strut measurement and feedback device 204 can provide any data including, for example, any measurement data determined at block 1404, any identification data determined at block 1402, etc. to the user device 206. The measurement data can include any type of data including captured image data. The measurement data can be transmitted wirelessly to the user device 206. Alternatively, the measurement data can be transmitted via a wire connected to the user device 206.

At block 1408, the strut measurement and feedback device 204, the remote device 208, or the user device 206 can compare the measurement data provided by the strut measurement and feedback device 204 at block 1406 to a predetermined prescription for the use of the external fixator 202. The prescription can be stored in memory of the device to perform the comparison such as the memory 314 of the strut measurement and feedback device 204, in memory of the remote device 208, and/or in memory on the user device 206. For embodiments in which the user device 206 performs the comparison, the user device 206 can determine if the adjusted length of the strut matches a prescribed length of the strut. The user device 206 can provide real-time feedback to an individual making the adjustments such as one or more indications or signals based on the comparison of the adjusted length of the strut to the proper length of the strut. For example, if the adjusted length matches the proper length, then a first type of indication can be provided by the user device 206. If the adjusted length does not match the proper length, then a second type of indication can be provided by the user device 206. The first and second types of indications can be any combination of visual, audible, or haptic indicators. In other embodiments, the strut measurement and feedback device 204 or the remote device 208 may perform the comparison and determine if the adjusted length of the strut matches a prescribed length of the strut. In many embodiments, the strut measurement and feedback device 204 or the remote device 208 may provide real-time feedback to an individual, via the strut measurement and feedback device 204 and/or the user device 206, by communicating the results of the comparison and/or providing one or more indications or signals based on the comparison of the adjusted length of the strut to the proper length of the strut.

At block 1410, based on the feedback provided by the user device 206, further adjustment can be made to the strut. Alternatively, if the strut length complies with the prescription, then the strut measurement and feedback device 204 can be attached to another strut of the external fixator and blocks 1402-1410 can be repeated.

While the present disclosure refers to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments, but that it has the full scope defined by the language of the following claims, and equivalents thereof. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

The foregoing discussion has been presented for purposes of illustration and description and is not intended to limit the disclosure to the form or forms disclosed herein. For example, various features of the disclosure are grouped together in one or more embodiments or configurations for the purpose of streamlining the disclosure. However, it should be understood that various features of the certain embodiments or configurations of the disclosure may be combined in alternate embodiments, or configurations. Moreover, the following claims are hereby incorporated into this Detailed Description by this reference, with each claim standing on its own as a separate embodiment of the present disclosure.

As used herein, an element or step recited in the singular and proceeded with the word "a" or "an" should be understood as not excluding plural elements or steps, unless such exclusion is explicitly recited. Furthermore, references to "one embodiment" of the present disclosure are not intended to be interpreted as excluding the existence of additional embodiments that also incorporate the recited features.

The phrases "at least one", "one or more", and "and/or", as used herein, are open-ended expressions that are both conjunctive and disjunctive in operation. The terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. All rotational references describe relative movement between the various elements. Identification references (e.g., primary, secondary, first, second, third, fourth, etc.) are not intended to connote importance or priority but are used to distinguish one feature from another. The drawings are for purposes of illustration only and the dimensions, positions, order and relative to sizes reflected in the drawings attached hereto may vary.

The invention claimed is:

1. An external bone alignment device arranged and configured to align two or more bones or pieces of bone, the device comprising:
  a first bone coupling device arranged and configured to engage a patient's first bone or piece of bone;
  a second bone coupling device arranged and configured to engage a patient's second bone or piece of bone;
  a plurality of struts coupled to the first and second bone coupling devices, each of the plurality of struts being arranged and configured to be lengthened and shortened so that adjustment of the strut moves the first bone coupling device relative to the second bone coupling device; and
  a strut measurement and feedback device arranged and configured to:
    selectively attach, at a plurality of attachment points, to one of the plurality of struts; and
    in real time, determine and provide information regarding an absolute or relative positioning or length of the strut to which the strut measurement and feedback device is attached.

2. The bone alignment device of claim 1, wherein the strut measurement and feedback device includes a communication interface arranged and configured to communicate with a remote device to provide real-time feedback to an individual as the length of the strut to which the device is attached is being adjusted to ensure the length adjustment complies with a prescription for the length of the strut.

3. The bone alignment device of claim 1, wherein the strut measurement and feedback device is arranged and configured to identify the strut to which it is attached from the plurality of struts.

4. The bone alignment device of claim 1, wherein the strut measurement and feedback device can determine if a length adjustment to the strut to which it is attached is correct.

5. The bone alignment device of claim 1, wherein the strut measurement and feedback device includes:
  a coupling component arranged and configured to enable the strut measurement and feedback device to be selectively attached and detached from one of the plurality of struts;
  a strut measurement component for providing real-time information regarding an absolute or relative positioning or length of the strut to which the strut measurement and feedback device is attached; and
  a communications interface arranged and configured to provide measurement data to a user device to provide real-time feedback regarding adjustments to the length of the strut to an individual making the adjustments.

6. The bone alignment device of claim 5, wherein the strut measurement component is also arranged and configured to determine the strut, from the plurality of struts, to which the strut measurement and feedback device is attached.

7. The bone alignment device of claim 5, wherein the communications interface is also arranged and configured to provide identification data regarding the strut to a user device to provide real-time feedback regarding adjustments to the length of the strut to which the strut measurement and feedback device is attached.

8. The bone alignment device of claim 5, wherein the strut measurement component is a camera arranged and configured to read visualizing markings positioned on the strut to which the strut measurement and feedback device is attached, the visualizing markings determining a length of the strut.

9. The bone alignment device of claim 8, wherein the strut measurement component is a scanner for reading a barcode positioned on the strut to which the strut measurement and feedback device is attached, the barcode identifying the strut to which the strut measurement and feedback device is attached.

10. The bone alignment device of claim 9, wherein the strut measurement component includes a radio-frequency identification (RFID) scanner for reading an RFID tag positioned on the strut to which the strut measurement and feedback device is attached, the RFID tag identifying the strut to which the strut measurement and feedback device is attached.

11. The bone alignment device of claim 5, wherein the communications interface component includes a wireless communications interface for transmitting measurement data and identification data regarding the strut to which the strut measurement and feedback device is attached to the user device.

12. The bone alignment device of claim 5, wherein the strut measurement and feedback device includes a device to adjust a length of the strut to which the strut measurement and feedback device is attached.

13. The bone alignment device of claim 12, wherein the device to adjust the length of the strut is arranged and configured to be removably attached to the strut measurement and feedback device.

14. The bone alignment device of claim 5, wherein the strut measurement and feedback device is arranged and configured to detect an adjustment made to the strut to which the strut measurement and feedback device is attached, the adjustment information including one of providing an initial length of the strut prior to adjustment and an ending length of the strut after the adjustment, and a measure of the change in length of the strut resulting from the adjustment.

15. The bone alignment device of claim 5, further comprising the user device arranged and configured to compare the adjustment to the strut to a predetermined prescription for adjusting the strut and indicating to an individual implementing the adjustment whether or not the proper strut was adjusted or whether or not the adjusted length of the strut is correct.

16. The device of claim 1, wherein the strut measurement and feedback device is arranged and configured to, in real-time, receive and trigger execution of one or more adjustment instructions determined based on the provided information.

17. A device to measure and provide feedback associated with an external bone alignment device comprising:
  a coupling component arranged and configured to selectively attach to one of a plurality of struts of the external bone alignment device, the external bone alignment device arranged and configured to align two or more bones or pieces of bone, the external bone alignment device comprising a first bone coupling device arranged and configured to engage a patient's first bone or piece of bone, a second bone coupling device arranged and configured to engage a patient's second bone or piece of bone, the plurality of struts coupled to the first and second bone coupling devices, each of the plurality of struts being arranged and configured to be lengthened and shortened so that adjustment of the strut moves the first bone coupling device relative to the second bone coupling device; and circuitry to, in real time, determine and provide information regarding an absolute or relative positioning or length of the strut to which the strut measurement and feedback device is attached.

18. The device of claim 17, wherein the circuitry includes a communication interface arranged and configured to communicate with a remote device to provide real-time feedback to an individual as the length of the strut to which the device is attached is being adjusted to ensure the length adjustment complies with a prescription for the length of the strut.

19. The device of claim 17, wherein the circuitry is arranged and configured to identify the strut to which it is attached from the plurality of struts.

20. The device of claim 17, wherein the circuitry can determine if a length adjustment to the strut to which it is attached is correct.

21. The device of claim 17, wherein the circuitry includes:
the coupling component arranged and configured to enable the strut measurement and feedback device to be selectively attached and detached from one of the plurality of struts;
a strut measurement component for providing real-time information regarding an absolute or relative positioning or length of the strut to which the strut measurement and feedback device is attached; and
a communications interface arranged and configured to provide measurement data to a user device to provide real-time feedback regarding adjustments to the length of the strut to an individual making the adjustments.

22. The device of claim 21, wherein the strut measurement component is also arranged and configured to determine the strut, from the plurality of struts, to which the circuitry is attached.

23. The device of claim 21, wherein the communications interface is also arranged and configured to provide identification data regarding the strut to a user device to provide real-time feedback regarding adjustments to the length of the strut to which the circuitry is attached.

24. The device of claim 21, wherein the strut measurement component is a camera arranged and configured to read visualizing markings positioned on the strut to which the circuitry is attached, the visualizing markings determining a length of the strut.

25. The device of claim 24, wherein the strut measurement component is a scanner for reading a barcode positioned on the strut to which the circuitry is attached, the barcode identifying the strut to which the circuitry is attached.

26. The device of claim 25, wherein the strut measurement component includes a radio-frequency identification (RFID) scanner for reading an RFID tag positioned on the strut to which the circuitry is attached, the RFID tag identifying the strut to which the circuitry is attached.

27. The device of claim 21, wherein the communications interface component includes a wireless communications interface for transmitting measurement data and identification data regarding the strut to which the circuitry is attached to the user device.

28. The device of claim 21, wherein the circuitry includes a device to adjust a length of the strut to which the circuitry is attached.

29. The device of claim 28, wherein the device to adjust the length of the strut is arranged and configured to be removably attached to the circuitry.

30. The device of claim 21, wherein the circuitry is arranged and configured to detect an adjustment made to the strut to which the circuitry is attached, the adjustment information including one of providing an initial length of the strut prior to adjustment and an ending length of the strut after the adjustment, and a measure of the change in length of the strut resulting from the adjustment.

31. The device of claim 17, wherein the circuitry is arranged and configured to, in real-time, receive and trigger execution of one or more adjustment instructions determined based on the provided information.

* * * * *